US012251094B1

(12) United States Patent
Deland

(10) Patent No.: US 12,251,094 B1
(45) Date of Patent: Mar. 18, 2025

(54) ACHILLES TENDON REPAIR SYSTEMS AND METHODS

(71) Applicant: Jonathan T. Deland, New York, NY (US)

(72) Inventor: Jonathan T. Deland, New York, NY (US)

(*) Notice: Subject to any disclaimer, the term of this patent is extended or adjusted under 35 U.S.C. 154(b) by 0 days.

(21) Appl. No.: 18/764,574

(22) Filed: Jul. 5, 2024

Related U.S. Application Data

(60) Provisional application No. 63/539,515, filed on Sep. 20, 2023.

(51) Int. Cl.
*A61B 17/04* (2006.01)

(52) U.S. Cl.
CPC ...... *A61B 17/0401* (2013.01); *A61B 17/0482* (2013.01)

(58) Field of Classification Search
CPC . A61B 17/04; A61B 17/0469; A61B 17/0482; A61B 17/0401
See application file for complete search history.

(56) References Cited

U.S. PATENT DOCUMENTS

| | | | |
|---|---|---|---|
| 5,496,341 A | 3/1996 | Sauer et al. | |
| 5,931,869 A | 8/1999 | Boucher et al. | |
| 6,129,729 A | 10/2000 | Snyder | |
| 9,622,741 B2 | 4/2017 | Levine | |
| 11,896,215 B2 | 2/2024 | Deland | |
| 2007/0198037 A1* | 8/2007 | Deland | A61B 17/0482 606/148 |
| 2014/0163583 A1* | 6/2014 | Rush | A61B 17/0469 606/144 |
| 2022/0022865 A1* | 1/2022 | Deland | A61B 17/0487 |

OTHER PUBLICATIONS

Clanton et al., "A Biomechanical Comparison of an Open Repair and 3 Minimally Invasive Percutaneous Achilles Tendon Repair Techniques During a Simulated, Progressive Rehabilitation Protocol", Am J Sports Med 2015 43: 1957-1964, (Jun. 2015) http://ajs.sagepub.com/content/43/8/1957.

* cited by examiner

*Primary Examiner* — Dianne Dornbusch
(74) *Attorney, Agent, or Firm* — David Meibos; Maywood IP Law

(57) ABSTRACT

A method for surgical repair of an Achilles tendon may include positioning an instrument proximate the Achilles tendon. The instrument may include a handle and a plurality of tendon guides. The method may also include maneuvering the instrument such that the plurality of tendon guides is positioned anteriorly, posteriorly, laterally, and medially of the Achilles tendon, actuating the plurality of tendon guides to retain the Achilles tendon between the plurality of tendon guides, and using the instrument to insert a suture through the Achilles tendon along one or more trajectories, each of which is offset at least 10° from a coronal plane.

20 Claims, 23 Drawing Sheets

ACHILLES TENDON REPAIR SYSTEMS AND METHODS

CROSS-REFERENCE TO RELATED APPLICATIONS

The present application claims the priority benefit of U.S. Provisional Patent Application No. 63/539,515, entitled ACHILLES TENDON REPAIR SYSTEMS AND METHODS, which was filed on Sep. 20, 2023, and is incorporated by reference as though set forth herein in its entirety.

TECHNICAL FIELD

The present disclosure relates generally to a devices and methods for tendon repair. Particularly, the present disclosed subject matter is directed towards devices and methods for improved targeting of the Achilles tendon and improved strength of Achilles tendon repair.

BACKGROUND

Current methods for minimally invasive Achilles tendon repair often lack precision devices to accurately target the tendon in specific planes during surgery. The ability to precisely target the tendon within a specific plane and at a specific angle is crucial for achieving optimal tendon alignment and tensioning, which are essential for successful repair and rehabilitation outcomes.

In traditional open surgery, surgeons have greater visibility and direct access to the Achilles tendon, allowing for manual manipulation and adjustment. However, in minimally invasive procedures, limited visualization and restricted access pose challenges for accurately targeting the tendon in specific planes and at specific angles.

Inadequate alignment and tensioning of the Achilles tendon can lead to complications such as tendon length discrepancy, altered biomechanics, and increased risk of re-rupture. Furthermore, suboptimal tendon positioning may hinder the effectiveness of subsequent rehabilitation efforts, prolonging recovery times and compromising functional outcomes for patients.

Therefore, there is a need in the field of orthopedic surgery for specialized devices and operating methods that enable surgeons to precisely target the Achilles tendon during minimally invasive repair procedures and achieve a repair strength comparable to that of open surgical tendon repair procedures.

SUMMARY

The various systems and methods of the present disclosure have been developed in response to the present state of the art, and in particular, in response to the problems and needs in the art that have not yet been fully solved by currently available devices and methods for Achilles tendon repair systems.

In some embodiments, a method for surgical repair of an Achilles tendon may include positioning an instrument proximate the Achilles tendon. The instrument may include a handle and a plurality of tendon guides. The method may also include maneuvering the instrument such that the plurality of tendon guides is positioned anteriorly, posteriorly, laterally, and medially of the Achilles tendon, actuating the plurality of tendon guides to retain the Achilles tendon between the plurality of tendon guides, and using the instrument to insert a suture through the Achilles tendon along one or more trajectories, each of which is offset at least 10° from a coronal plane.

In the method of any preceding paragraph, the plurality of tendon guides may include a medial tendon guide, a lateral tendon guide, an anterior tendon guide, and a posterior tendon guide. Maneuvering the instrument may further include positioning the medial tendon guide medially of the Achilles tendon, positioning the lateral tendon guide laterally of the Achilles tendon, positioning the anterior tendon guide anteriorly of the Achilles tendon, and positioning the posterior tendon guide posteriorly of the Achilles tendon.

In the method of any preceding paragraph, each of the one or more trajectories may be offset at least 20° from the coronal plane.

In the method of any preceding paragraph, the method may further include using the instrument to insert one or more sutures through the Achilles tendon such that the one or more sutures are routed according to a suturing technique used in open Achilles tendon repair surgery.

In the method of any preceding paragraph, the suturing technique may be a Krackow suturing technique.

In the method of any preceding paragraph, the instrument may also include a posterior pin guide including one or more posterior pin holes.

In the method of any preceding paragraph, each of the one or more posterior pin holes may be angularly offset from the coronal plane and may be parallel to at least one of the one or more trajectories.

In the method of any preceding paragraph, the posterior pin guide further may include a lateral pin guide and a medial pin guide that guide a pin parallel to the coronal plane.

In the method of any preceding paragraph, the method may also include inserting one or more pins through the one or more posterior pin holes and into the Achilles tendon along directions that are at least partially anterior.

In some embodiments, a method for surgical repair of an Achilles tendon may include positioning an instrument proximate the Achilles tendon. The instrument may include a handle, a medial tendon guide, a lateral tendon guide, an anterior tendon guide, a posterior tendon guide, and a posterior pin guide having one or more posterior pin holes. The method may also include maneuvering the instrument to receive the Achilles tendon such that the Achilles tendon is retained between the medial tendon guide and the lateral tendon guide and actuating the anterior tendon guide to grip the Achilles tendon between the posterior tendon guide and the anterior tendon guide.

In the method of any preceding paragraph, the method may also include inserting one or more pins through the one or more posterior pin holes and into the Achilles tendon along directions that are at least partially anterior.

In the method of any preceding paragraph, the method may also include maneuvering the instrument to receive the Achilles tendon such that the Achilles tendon is retained between the medial tendon guide and the lateral tendon guide at a first location, actuating the anterior tendon guide to grip the Achilles tendon between the posterior tendon guide and the anterior tendon guide at the first location, using the instrument to insert a first suture through the Achilles tendon along one or more trajectories, releasing the Achilles tendon from the instrument, partially withdrawing the instrument so that the posterior pin guide is located between the first suture and a percutaneous incision, maneuvering the instrument to receive the Achilles tendon such that the Achilles tendon is retained between the medial tendon guide and the lateral tendon guide at a second location, and using the instrument to insert a second suture through the Achilles tendon along one or more trajectories.

In the method of any preceding paragraph, each of the one or more trajectories may be offset at least 10° from a coronal plane.

In the method of any preceding paragraph, each of the one or more trajectories may be offset at least 15° from a coronal plane In the method of any preceding paragraph, the method may also include using the instrument to insert one or more sutures through the Achilles tendon such that the one or more sutures are routed according to a Krackow suturing technique.

In some embodiments, a method for surgical repair of an Achilles tendon may include positioning an instrument proximate the Achilles tendon. The instrument may include a handle, a plurality of tendon guides, and at least one pin guide selected from a group consisting of a lateral pin guide and a medial pin guide. The method may also include maneuvering the instrument such that the plurality of tendon guides is positioned anteriorly, posteriorly, laterally, and medially of the Achilles tendon, actuating the plurality of tendon guides to retain the Achilles tendon between the plurality of tendon guides, and inserting one or more pins through one or more pin holes of the pin guide and into the Achilles tendon along an at least partially anterior direction offset from a coronal plane by at least 10° or an at least partially posterior direction offset by the coronal plane by at least 10°.

In the method of any preceding paragraph, the plurality of tendon guides may include a medial tendon guide, a lateral tendon guide, an anterior tendon guide, and a posterior tendon guide. Maneuvering the instrument may further include positioning the medial tendon guide medially of the Achilles tendon, positioning the lateral tendon guide laterally of the Achilles tendon, positioning the anterior tendon guide anteriorly of the Achilles tendon, and positioning the posterior tendon guide posteriorly of the Achilles tendon.

In the method of any preceding paragraph, at least one of the one or more pin holes may be positioned anterior to the coronal plane and an axis of the at least one of the one or more pin holes may be posteriorly offset from the coronal plane by at least 10°.

In the method of any preceding paragraph, at least one of the one or more pin holes may be positioned posterior to the coronal plane and an axis of the at least one of the one or more pin holes may be anteriorly offset from the coronal plane by at least 10°.

In the method of any preceding paragraph, the method may also include using the one or more pins to guide one or more sutures through the Achilles tendon along the at least partially anterior direction or the at least partially posterior direction.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

DETAILED DESCRIPTION

Figure 1:
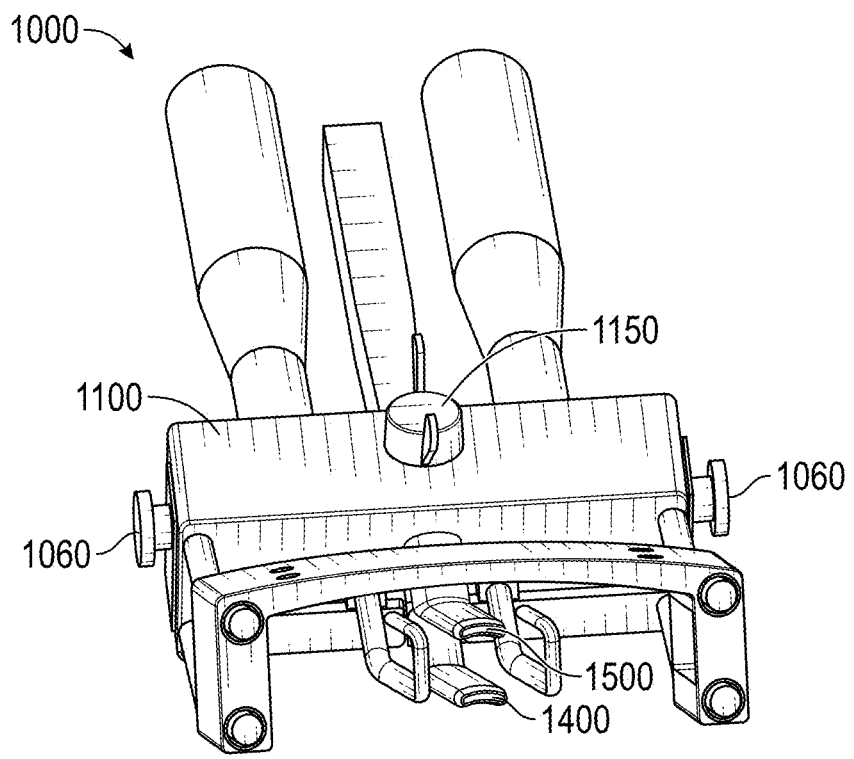
FIG. 1 is a perspective view of an instrument for surgical repair of an Achilles tendon according to an embodiment.
Figure 2:
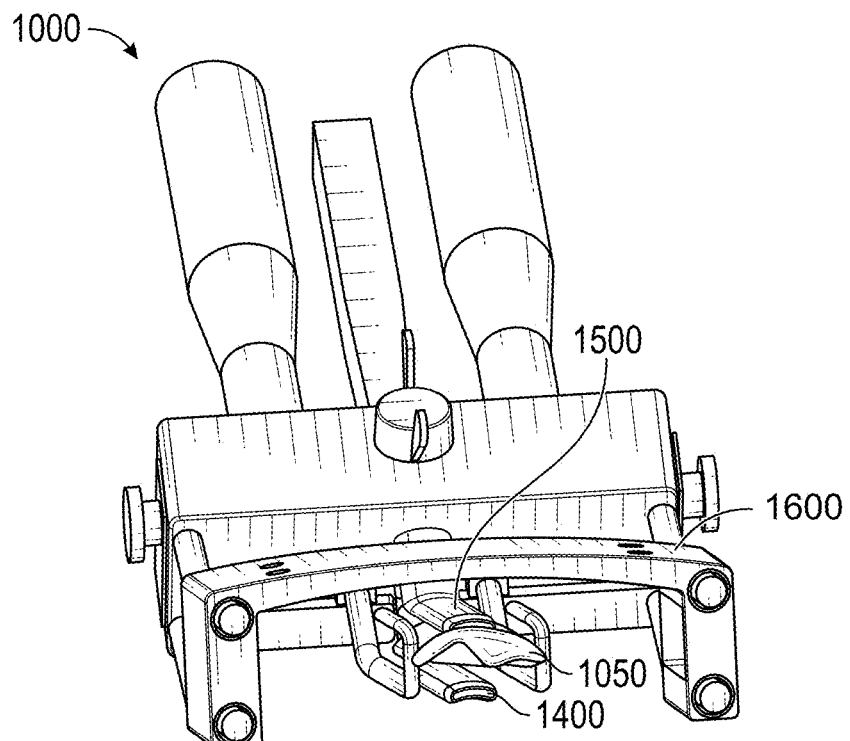
FIG. 2 is a perspective view of the instrument for surgical repair of an Achilles tendon of FIG. 1 engaging a tendon with an anterior tendon guide in an open position.
Figure 3:
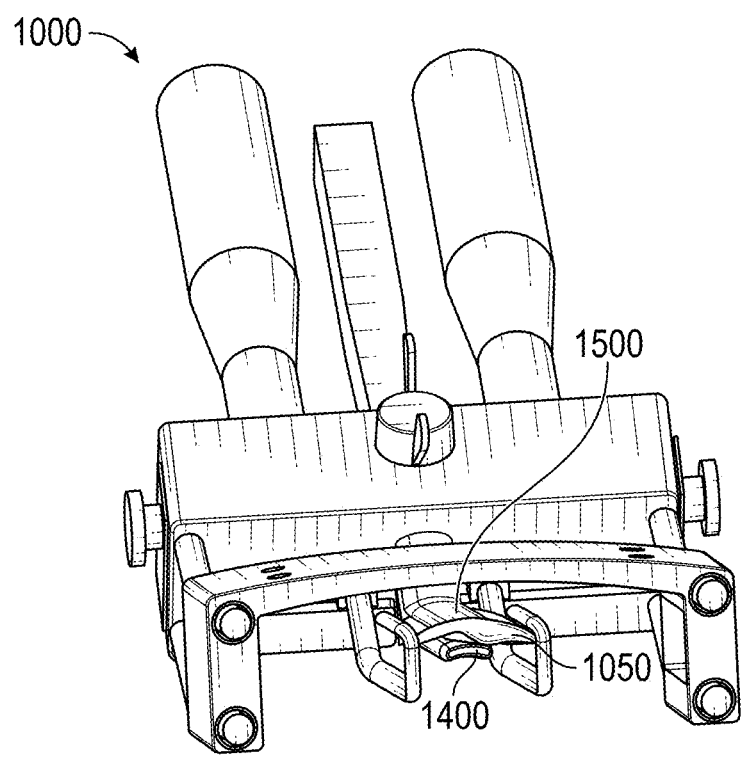
FIG. 3 is a perspective view of the instrument for surgical repair of an Achilles tendon of FIG. 1 engaging a tendon with an anterior tendon guide in a closed position.
Figure 4:
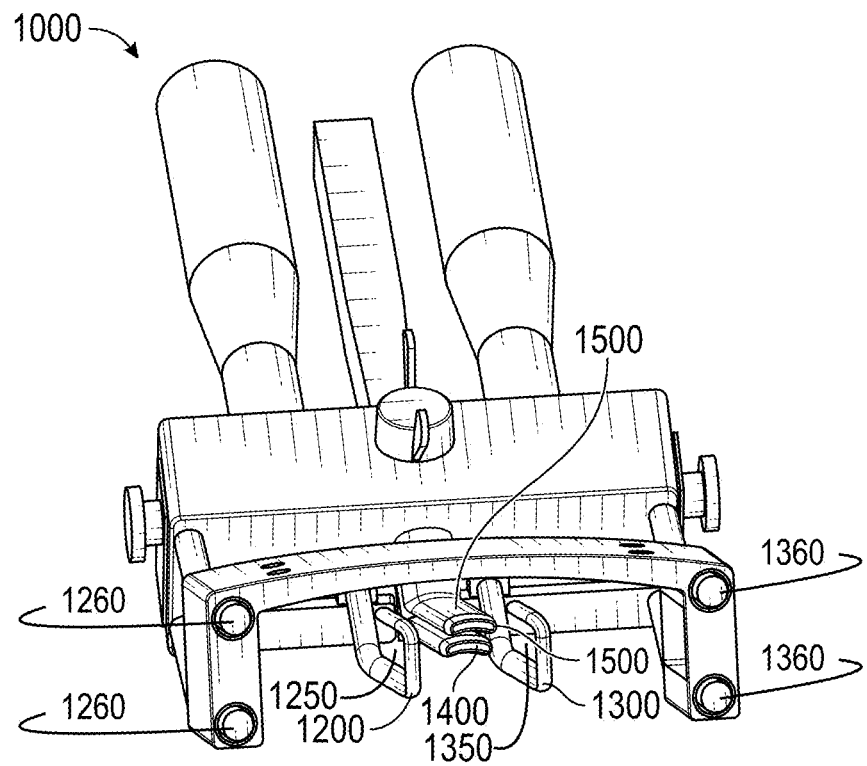
FIG. 4 is a perspective view of the instrument for surgical repair of an Achilles tendon of FIG. 1 with an anterior tendon guide in a closed position.
Figure 5:
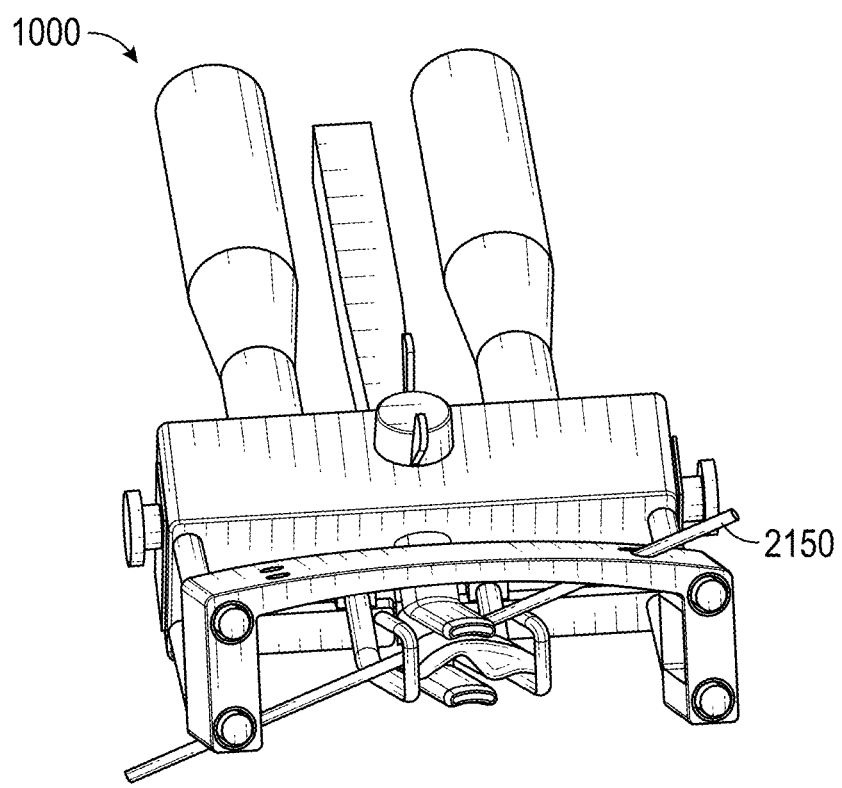
FIG. 5 is a perspective view of the instrument for surgical repair of an Achilles tendon of FIG. 1 engaging a tendon with an anterior tendon guide in a closed position and a suture needle engaging a tendon.
Figure 6:
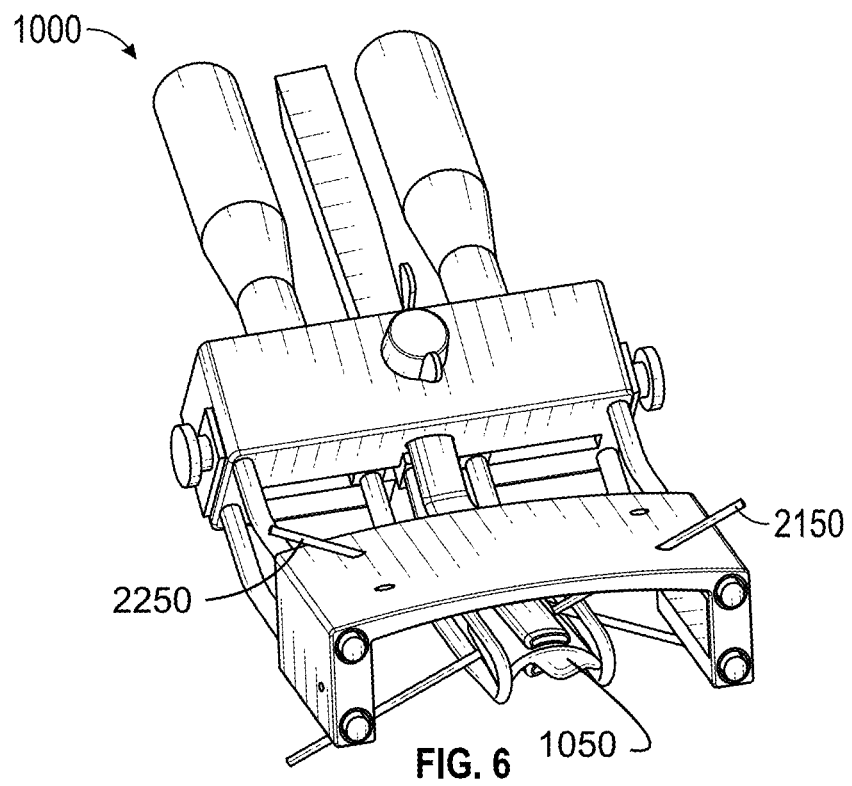
FIG. 6 is a perspective view of the instrument for surgical repair of an Achilles tendon of FIG. 1 engaging a tendon with an anterior tendon guide in a closed position and two suture needles engaging a tendon.
Figure 7:
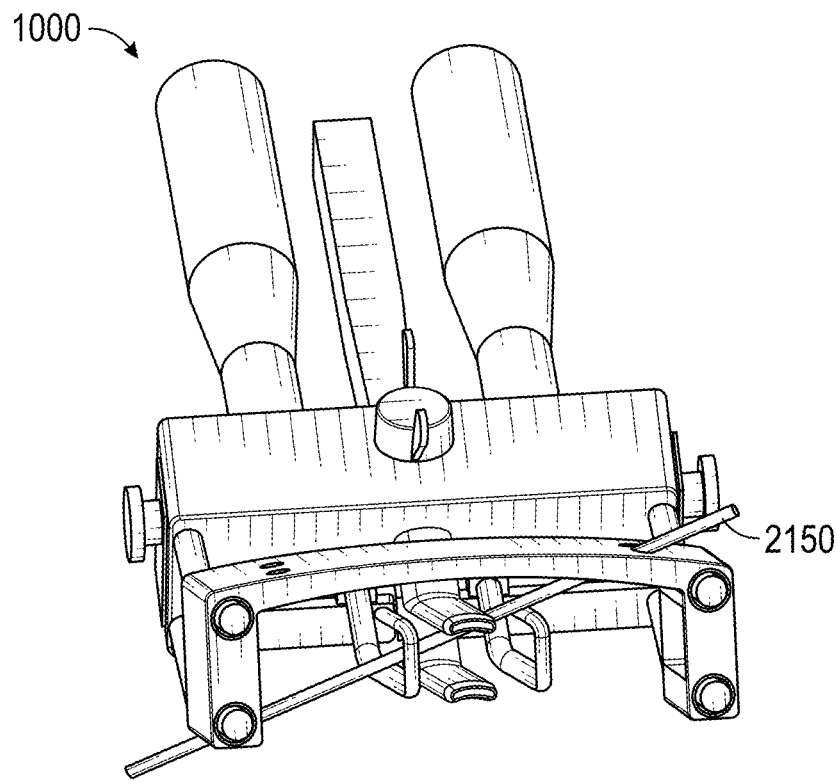
FIG. 7 is a perspective view of the instrument for surgical repair of an Achilles tendon of FIG. 1 in a closed position and with a suture needle.
Figure 8:
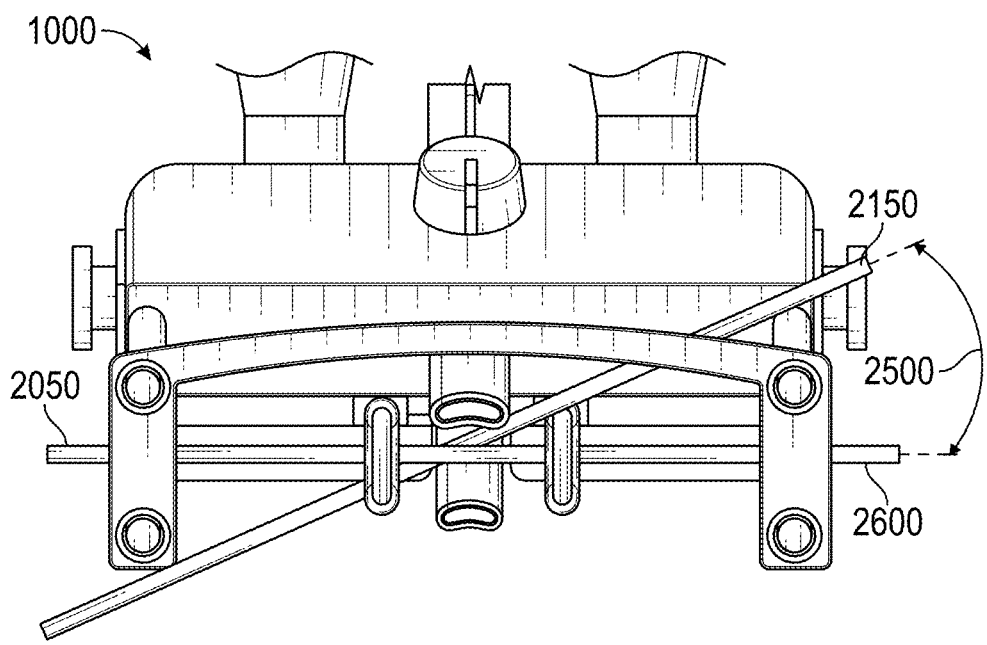
FIG. 8 is a partial perspective view of the instrument for surgical repair of an Achilles tendon of FIG. 1 in a closed position and with two suture needles.
Figure 9:
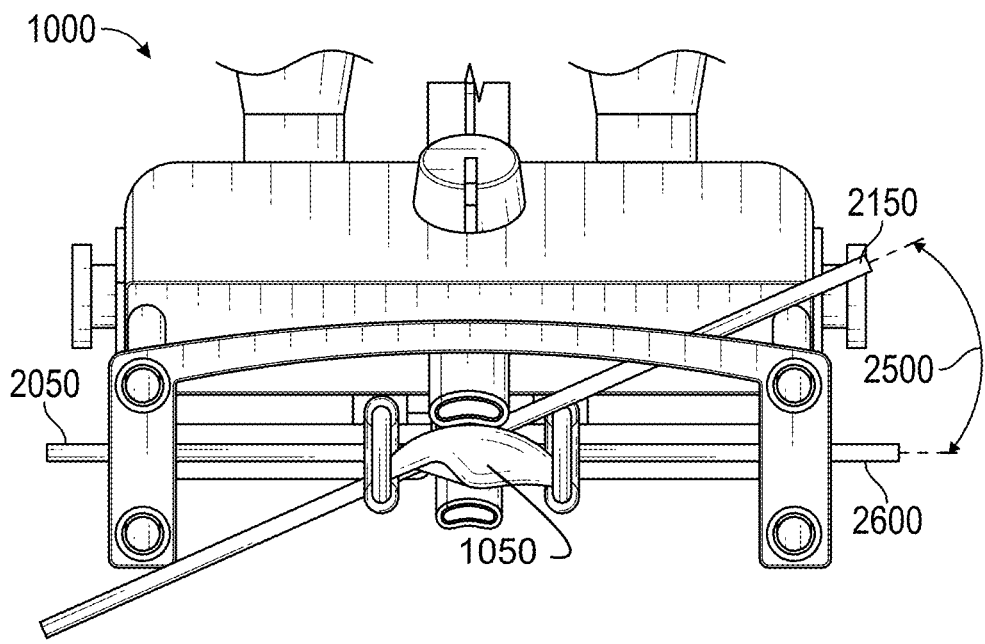
FIG. 9 is a perspective view of the instrument for surgical repair of an Achilles tendon of FIG. 1 engaging a tendon with an anterior tendon guide in a closed position and two suture needles engaging a tendon.
Figure 10:
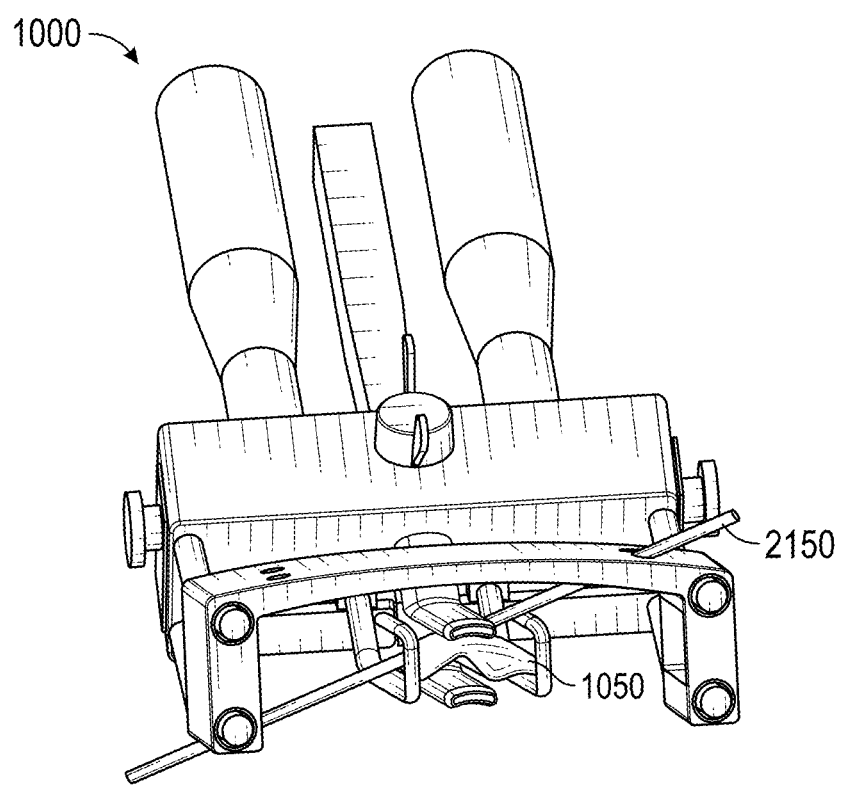
FIG. 10 is a perspective view of the instrument for surgical repair of an Achilles tendon of FIG. 1 engaging a tendon with an anterior tendon guide in a closed position and a suture needle engaging a tendon.
Figure 11:
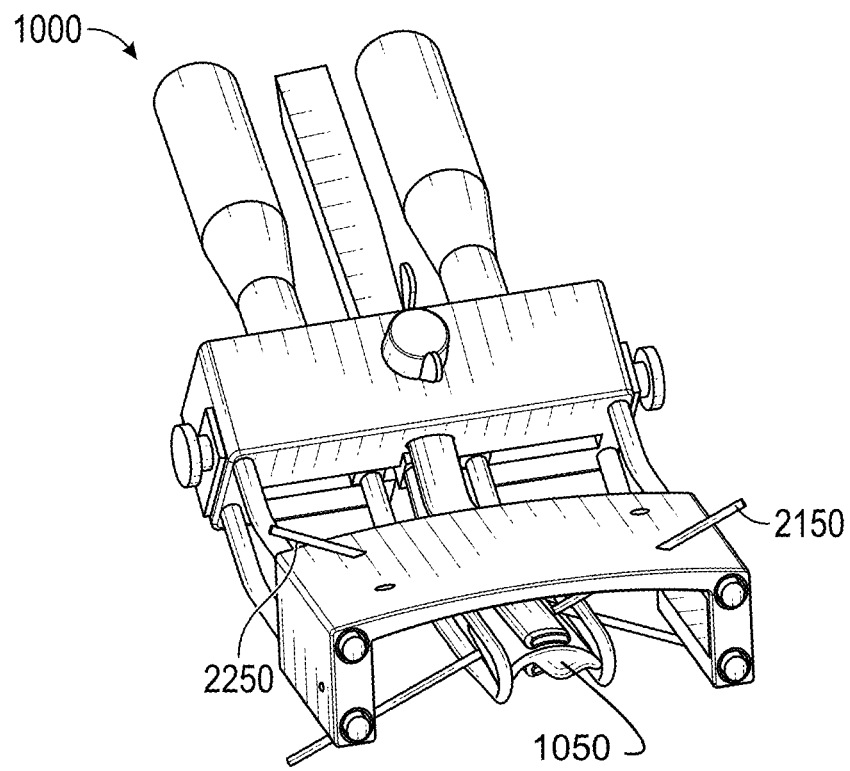
FIG. 11 is a perspective view of the instrument for surgical repair of an Achilles tendon of FIG. 1 engaging a tendon with an anterior tendon guide in a closed position and two suture needles engaging a tendon.
Figure 12:
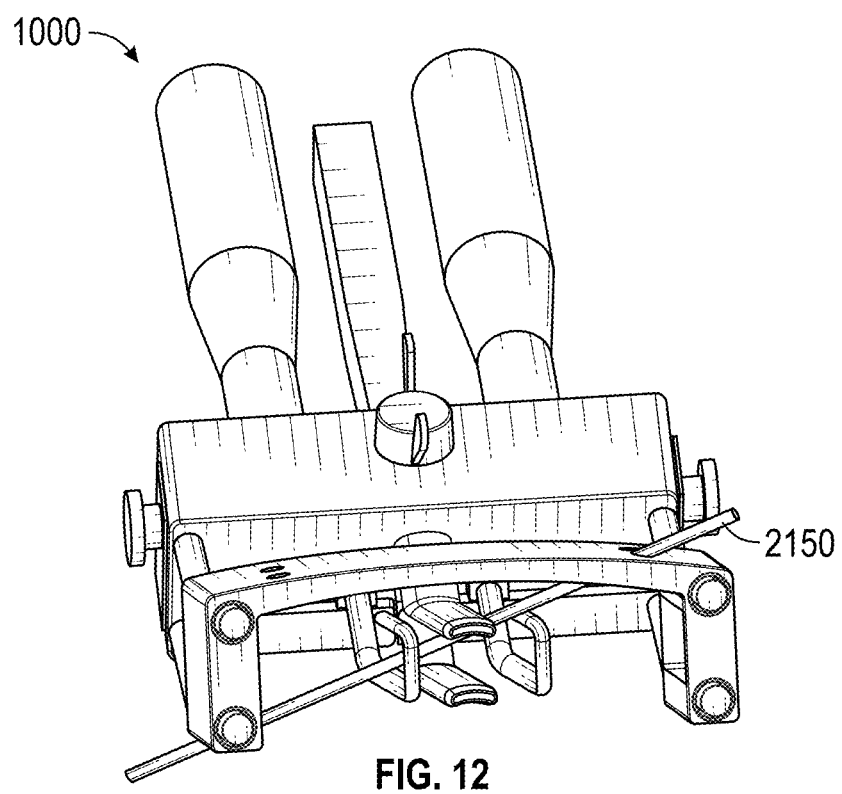
FIG. 12 is a perspective view of the instrument for surgical repair of an Achilles tendon of FIG. 1 with a suture needle.
Figure 13:
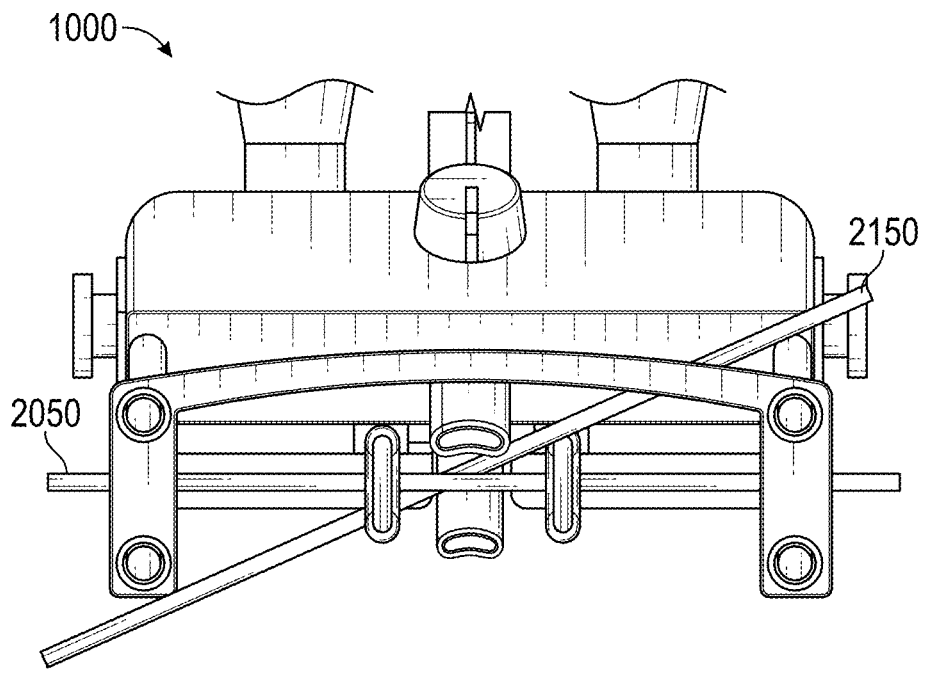
FIG. 13 is a perspective view of the instrument for surgical repair of an Achilles tendon of FIG. 1 with two suture needles.
Figure 14:
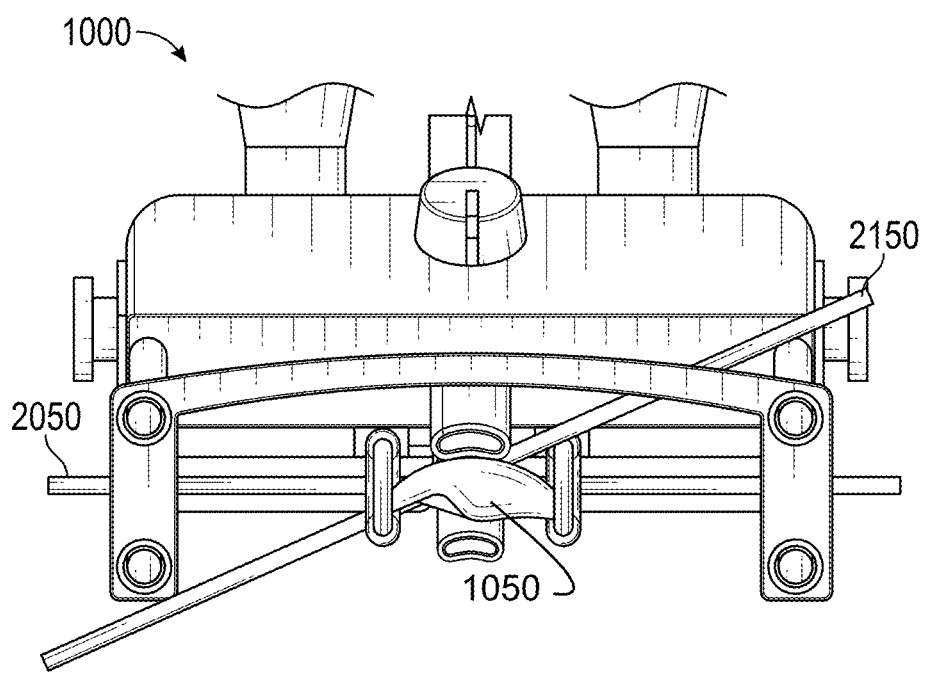
FIG. 14 is a perspective view of the instrument for surgical repair of an Achilles tendon of FIG. 1 engaging a tendon with an anterior tendon guide in a closed position and two suture needles engaging a tendon.
Figure 15:
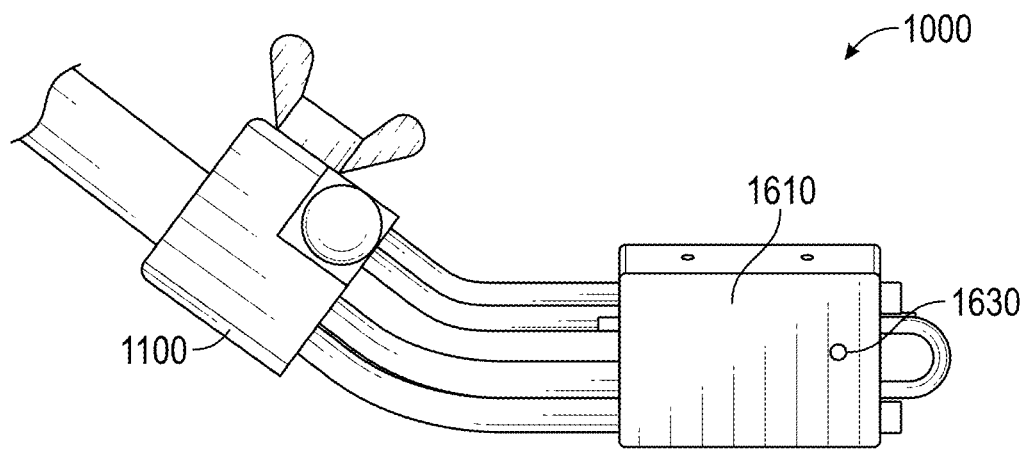
FIG. 15 is a partial side view of the instrument for surgical repair of an Achilles tendon of FIG. 1.
Figure 16:
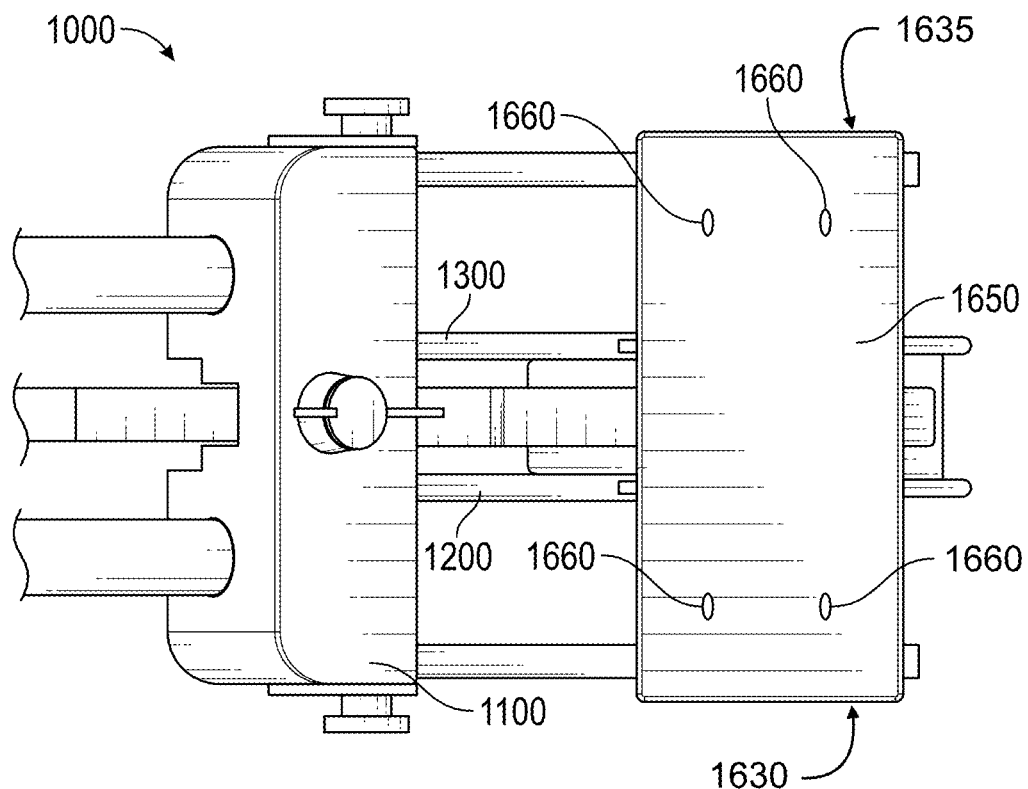
FIG. 16 is a partial top view of the instrument for surgical repair of an Achilles tendon of FIG. 1.
Figure 17:
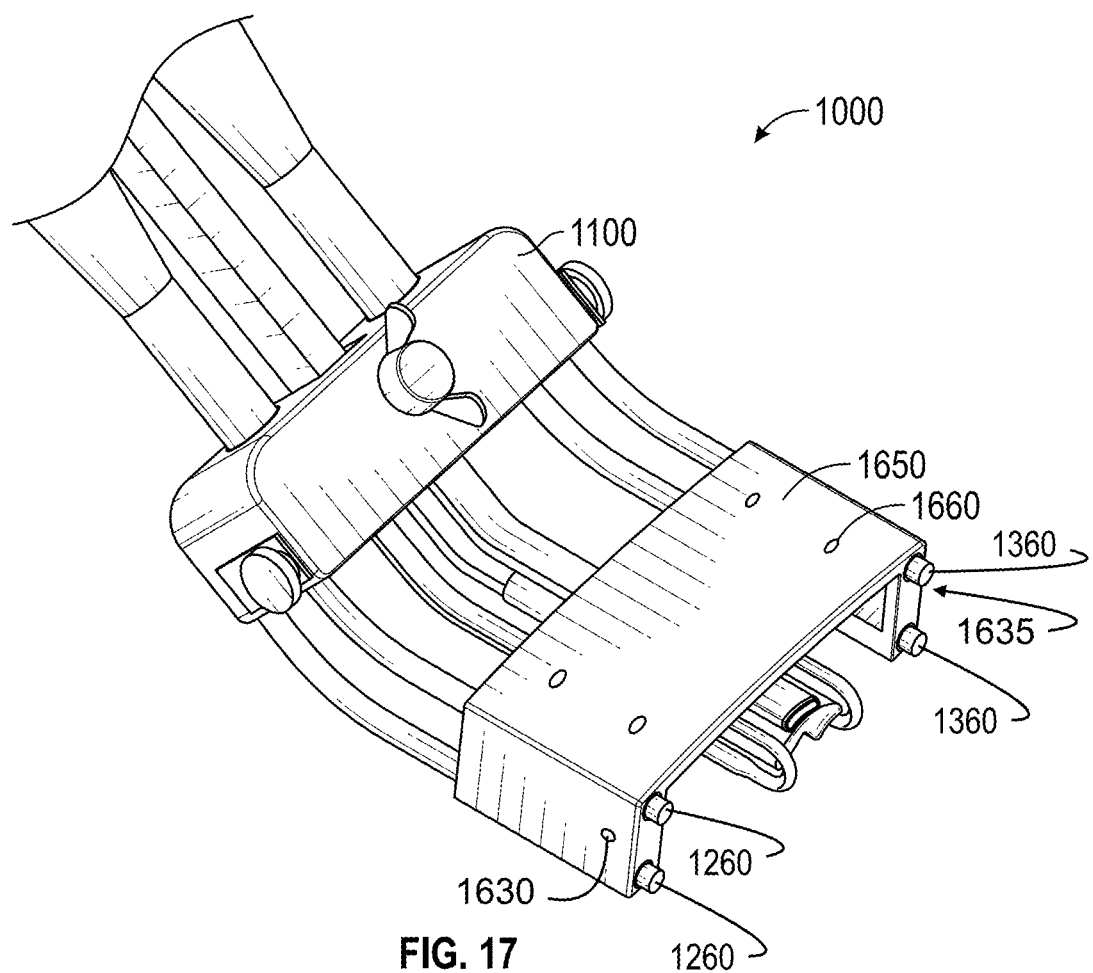
FIG. 17 is a partial perspective view of the instrument for surgical repair of an Achilles tendon of FIG. 1.
Figure 18:
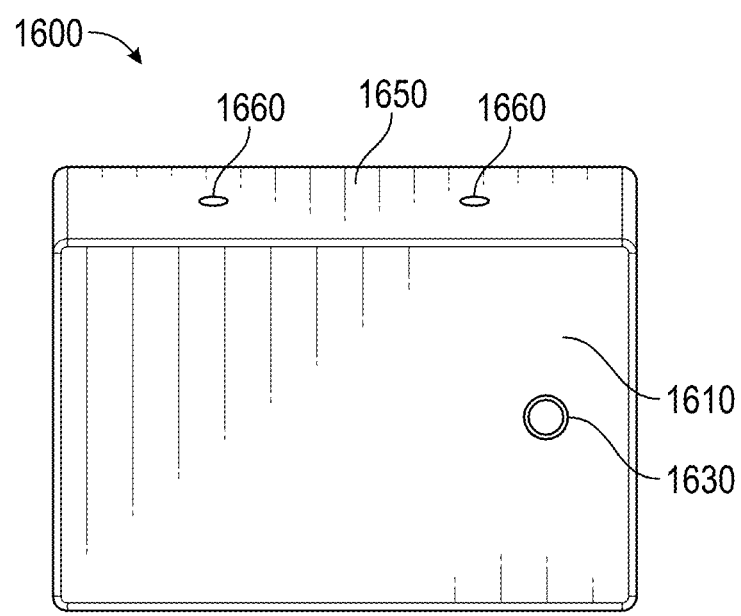
FIG. 18 is a perspective view of a suture guide housing of the instrument for surgical repair of an Achilles tendon of FIG. 1.
Figure 19:
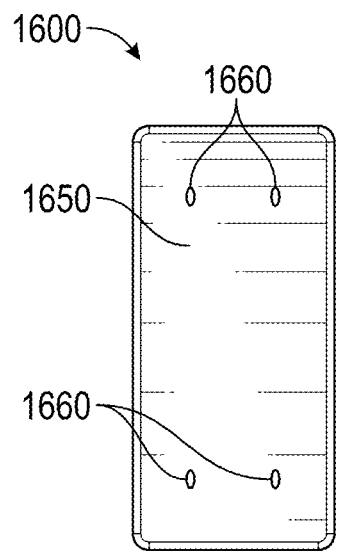
FIG. 19 is a top view of a suture guide housing of the instrument for surgical repair of an Achilles tendon of FIG. 1.
Figure 20:
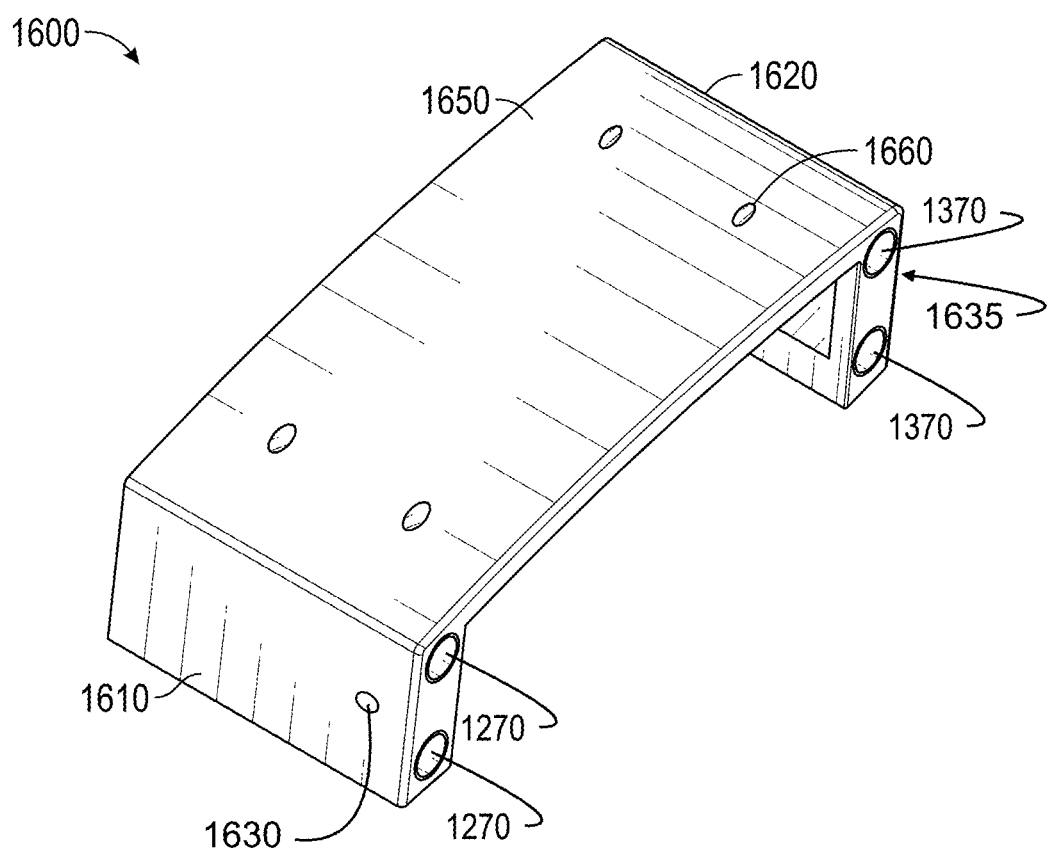
FIG. 20 is a perspective view of a suture guide housing of the instrument for surgical repair of an Achilles tendon of FIG. 1.
Figure 21:
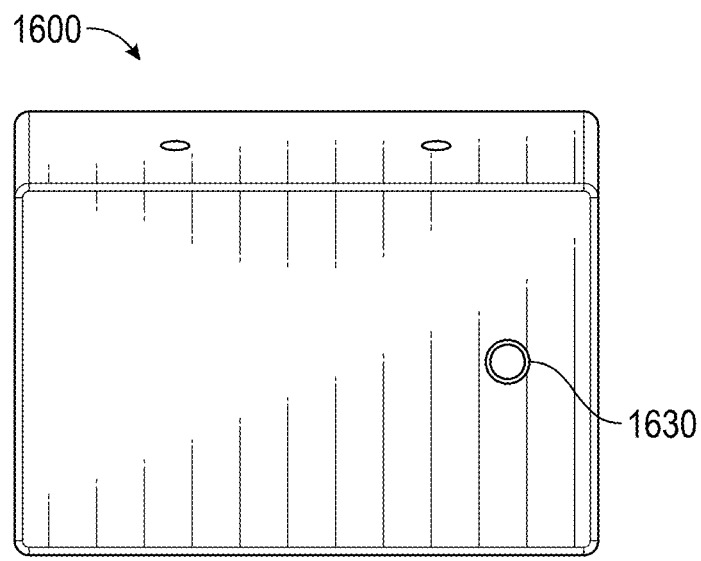
FIG. 21 is a perspective view of a suture guide housing of the instrument for surgical repair of an Achilles tendon of FIG. 1.
Figure 22:
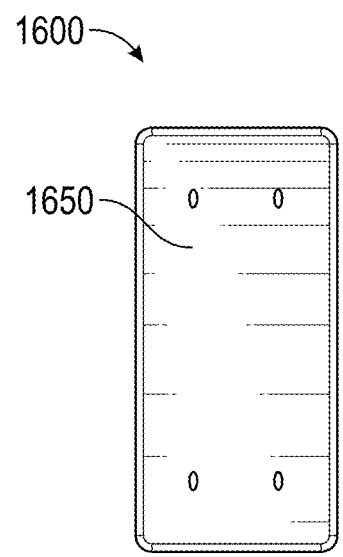
FIG. 22 is a top view of a suture guide housing of the instrument for surgical repair of an Achilles tendon of FIG. 1.
Figure 23:
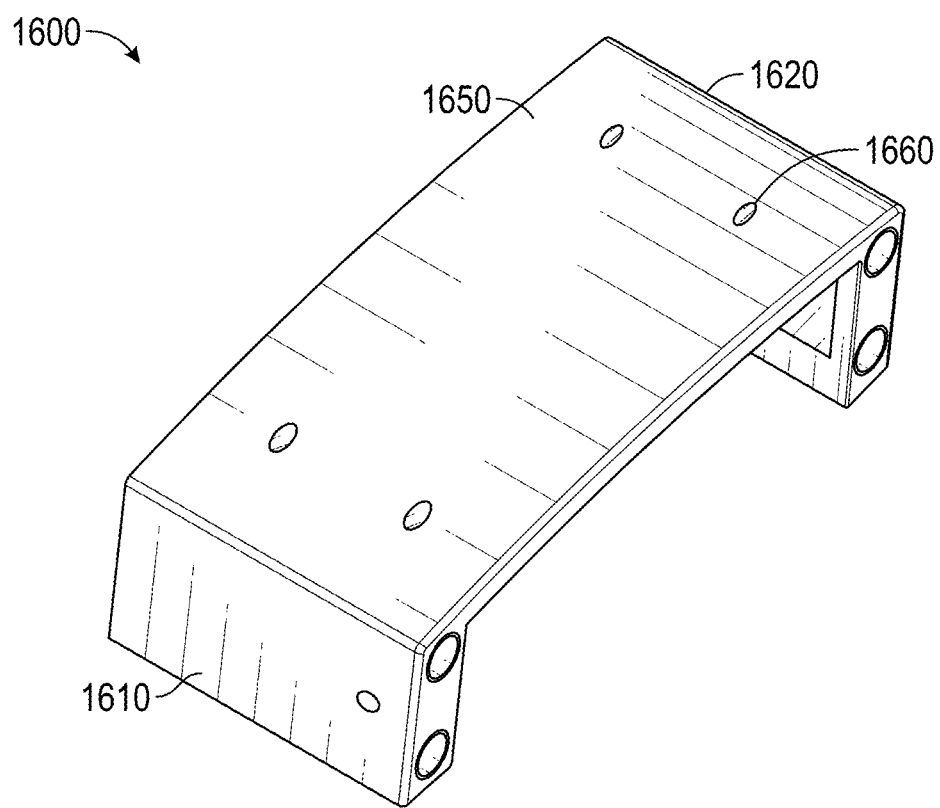
FIG. 23 is a perspective view of a suture guide housing of the instrument for surgical repair of an Achilles tendon of FIG. 1.

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 36, is not intended to limit the scope of the claims, but is merely representative of exemplary embodiments of the present disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Not every feature of each embodiment is labeled in every figure in which that embodiment appears, in order to keep the figures clear. Similar reference numbers (for example, those that are identical except for the first numeral) may be used to indicate similar features in different embodiments.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

Any of the devices described herein may be fabricated from metals, alloys, polymers, plastics, ceramics, glasses, composite materials, or combinations thereof, including but not limited to stainless steel, ABS, polycarbonate, glass filled polycarbonate, PEEK (polyether ether ketone), titanium, and titanium alloys, among others. Different materials may be used within a single part.

FIG. 1 through FIG. 14 are a perspective views of an instrument for surgical repair of an Achilles tendon or tendon repair instrument 1000 according to an embodiment. In some embodiments, tendon repair instrument 1000 may be configured for minimally invasive percutaneous Achilles tendon repair surgery. More specifically, the tendon repair instrument 1000 may be configured to engage an Achilles tendon in multiple planes.

The tendon repair instrument 1000 may have an interior portion configured to engaged the Achilles tendon within a body of a patient and an exterior portion that remains outside of the body of the patient. The interior portion may include a plurality of tendon guides. The exterior portion may include a handle and a posterior pin guide.

The tendon repair instrument 1000 may further be configured so that, when the interior portion of the device retains at least a portion of an Achilles tendon, the portion of the Achilles tendon has a generally fixed location with respect to the exterior portion of the device.

The tendon repair instrument 1000 may be configured for Achilles tendon repair of the Achilles tendon of a right leg and/or a left leg of a patient. The following descriptions of the tendon repair instrument 1000 and methods for surgical repair of an Achilles tendon may be directed towards repair of the Achilles tendon of the right leg of a patient.

For repair of an Achilles tendon of a left leg of a patient, the tendon repair instrument 1000 and methods for surgical repair of an Achilles tendon as described may be used, however, the descriptions of medial and lateral directions may be reversed. For example, for repair of the Achilles tendon of the right leg, lateral may indicate the right side of the patient and medial may indicate the left side of the patient. For repair of the Achilles tendon of the left leg, lateral may indicate the left side of the patient and medial may indicate the right side of the patient.

Alternatively, for repair of an Achilles tendon of a left leg of a patient, a mirror image of the tendon repair instrument 1000 as described may be used and the descriptions of medial and lateral directions may remain as described herein.

The tendon repair system may include similar instruments, and/or similar methods as described in U.S. Pat. No. 11,896,215 filed on 27 Jul. 2021, entitled "ACHILLES TENDON REPAIR DEVICE", the disclosure of which is incorporated herein by reference in its entirety.

The tendon repair system may further include similar instruments, and/or similar methods as described in U.S. Pat. No. 7,615,062 filed on 23 Apr. 2007, entitled "SUTURE GUIDE AND RUPTURED TISSUE REPAIR", the disclosure of which is incorporated herein by reference in its entirety.

The tendon repair instrument 1000 may include a handle 1100 and a plurality of tendon guides. The plurality of tendon guides may include a lateral tendon guide 1200; a medial tendon guide 1300; an anterior tendon guide 1400; and a posterior tendon guide 1500. The plurality of tendon guides may be configured to retain a tendon 1050 to facilitate passage of a plurality suture needles through the tendon 1050.

The handle 1100 may further include an anterior adjustment feature 1150 configured to be moveably coupled to the handle 1100 and further configured to adjust the position of a posterior tendon guide 1500 in an anterior-posterior plane. The handle 1100 may further include one or more medial-lateral adjustment features 1060 configured to be moveably couple to the handle 1100 and further configured to adjust the position of a lateral tendon guide 1200 and/or a medial tendon guide 1300 in a medial-lateral plane. The handle 1100 may further include a posterior pin guide 1600 including a first sidewall 1610; a second sidewall 1620; and a top surface 1650.

In an embodiment, a lateral tendon guide 1200 and a medial tendon guide 1300 may be configured and spaced apart such that a tendon 1050 may be retained between the lateral tendon guide 1200 and the medial tendon guide 1300. The spacing between the lateral tendon guide 1200 and the medial tendon guide 1300 may be adjusted with a medial-lateral adjustment feature 1060. The lateral tendon guide 1200 and the medial tendon guide 1300 may be configured so that the range of the distance the lateral tendon guide 1200 may be spaced apart from the medial tendon guide 1300 may be approximately 3 cm-12 cm. The distance the lateral tendon guide 1200 may be spaced apart from the medial tendon guide 1300 may be equal to or greater than the width of a posterior tendon guide 1500 and equal to or greater than the width of an anterior tendon guide 1400.

In an embodiment, a posterior tendon guide 1500 and an anterior tendon guide 1400 may be configured and spaced apart such that a tendon 1050 may be retained between the posterior tendon guide 1500 and the anterior tendon guide 1400. The anterior tendon guide 1400 may be movably coupled to the handle 1100 such that the anterior tendon guide 1400 may be actuated to grip the tendon 1050 between the anterior tendon guide 1400 and the posterior tendon guide 1500.

The spacing between the posterior tendon guide 1500 and the anterior tendon guide 1400 may be adjusted with an anterior adjustment feature 1150. The anterior tendon guide 1400 may be configured to be actuated to grip the tendon 1050 between the anterior tendon guide 1400 and the posterior tendon guide 1500. The posterior tendon guide 1500 and the anterior tendon guide 1400 may be configured so that the range of the distance the posterior tendon guide 1500 may be spaced apart from the anterior tendon guide 1400 is approximately 2 cm-10 cm.

The spacing of a lateral tendon guide 1200 and a medial tendon guide 1300 may be configured to be equal to or larger than the size of a tendon 1050, in a medial-lateral plane. Additionally, the spacing of the lateral tendon guide 1200 and the medial tendon guide 1300 may be configured to fit within a paratenon of a tendon 1050. The spacing of a posterior tendon guide 1500 and an anterior tendon guide 1400 may be configured to be equal to or larger than the size of a tendon 1050, in an anterior-posterior plane. Additionally, the spacing of the posterior tendon guide 1500 and the anterior tendon guide 1400 may be configured to fit within a paratenon of a tendon 1050.

In an embodiment, a lateral tendon guide 1200; a medial tendon guide 1300; an anterior tendon guide 1400; and a posterior tendon guide 1500 each may extend from a handle 1100 and may be configured to enter a paratenon of a tendon 1050 through a percutaneous incision to a depth of up to 25 cm.

FIG. 15 through FIG. 23 show partial side, partial top and perspective views of the instrument for surgical repair of an Achilles tendon or tendon repair instrument 1000 according to an embodiment. In an embodiment, a posterior pin guide 1600 may include a top surface 1650 that may include a plurality of posterior pin holes 1660. The posterior pin guide 1600 may further include a first sidewall 1610 and a second sidewall 1620. The first sidewall 1610 may include a medial pin guide 1635 and the second sidewall 1620 may include a lateral pin guide 1630. The lateral pin guide 1630 and medial pin guide 1635 may be configured to guide a first suture needle 2050 through the first sidewall 1610 and the second sidewall 1620 generally parallel to a coronal plane 2600.

The posterior pin guide 1600 may further include one or more medial arm apertures 1370 through the second side wall 1620 and one or more lateral arm apertures 1270 through the first side wall 1610. The handle 1100 may include one or more medial outer arms 1360 and one or more lateral outer arms 1260. The one or more medial arm apertures 1370 may be configured to slidably receive the one or more medial outer arms 1360. The one or more lateral arm apertures 1270 may be configured to slidably receive the one or more lateral outer arms 1260.

The posterior pin guide 1600 may be positioned along the one or more medial outer arms 1360 and the one or more lateral outer arms 1260 based on the desired suture trajectories through the Achilles tendon.

The lateral pin guide 1630 and medial pin guide 1635 may be configured to guide a first suture needle 2050 through a tendon 1050 between a posterior tendon guide 1500 and an anterior tendon guide 1400 with the tendon 1050 retained between the posterior tendon guide 1500 and the anterior tendon guide 1400. The lateral pin guide 1630 and medial pin guide 1635 may be located in a distal portion of a posterior pin guide 1600. The posterior pin guide 1600 may be positioned posterior to the tendon 1050 such that the posterior pin holes 1660 may be configured to guide insertion of one or more suture needles through the tendon 1050 along at least partially anterior directions.

In an embodiment, a lateral tendon guide 1200 may include a lateral tendon guide eye 1250 and a medial tendon guide 1300 may include a medial tendon guide eye 1350. The lateral tendon guide eye 1250 and the medial tendon guide eye 1350 may each be configured as a hook shape. The lateral tendon guide eye 1250 and the medial tendon guide eye 1350 may further be configured so the eye of the hook may be aligned with the spacing between a posterior tendon guide 1500 and an anterior tendon guide 1400. Additionally, the opening of each hook may be located at a proximal end of the lateral tendon guide 1200 and the medial tendon guide 1300.

In an embodiment, a top surface 1650 may include a plurality of posterior pin holes 1660 configured to guide a plurality of suture needles through a tendon 1050 between a posterior tendon guide 1500 and an anterior tendon guide 1400 with the tendon 1050 retained between the posterior tendon guide 1500 and the anterior tendon guide 1400. Each of the posterior pin holes 1660 may be configured to guide a suture needle: through a top surface 1650; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. In an embodiment, each of the posterior pin holes 1660 may be configured to have a suture needle trajectory angle 2500 that may be offset at least 10° from a coronal plane 2600.

In an embodiment, each of the posterior pin holes 1660 may be configured to have a suture needle trajectory angle 2500 that may be offset at least 15° from a coronal plane 2600. In an embodiment, each of the posterior pin holes 1660 may be configured to have a suture needle trajectory angle 2500 that may be offset at least 20° from a coronal plane 2600.

In an embodiment, a top surface 1650 may include four or more posterior pin holes 1660. The four or more posterior pin holes 1660 may be configured wherein half of the four or more posterior pin holes 1660 are mirrored about a central medial-lateral plane of the tendon repair instrument 1000. The four or more posterior pin holes 1660 may be configured to receive: a second suture needle 2150; a third suture needle 2250; a fourth suture needle 2350; and a fifth suture needle (not shown).

In an embodiment, a first suture needle 2050 may be configured to shuttle a first suture 2000: through a first sidewall 1610; through the skin and soft tissue of a patient; through one of a lateral tendon guide eye 1250 and a medial tendon guide eye 1350; through a tendon 1050, retained between the posterior tendon guide 1500 and the anterior tendon guide 1400, and retained between the lateral tendon guide 1200 and the medial tendon guide 1300; through the other of a lateral tendon guide eye 1250 and a medial tendon guide eye 1350; and exiting a patient through the soft tissue and skin. The first suture needle 2050 may be configured to disengage from the first suture 2000 leaving the ends of the first suture 2000 exterior to a patient and a central portion of the first suture 2000 tracing a path through the tendon repair instrument 1000.

In an embodiment, a second suture needle 2150 may be configured to shuttle a second suture 2100: through an posterior pin hole 1660, in a generally posterior to anterior direction; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. The second suture needle 2150 may be configured to disengage from the second suture 2100 leaving the ends of the second suture 2100 exterior to a patient and a central portion of the second suture 2100 tracing a path through the tendon repair instrument 1000.

In an embodiment, a third suture needle 2250 may be configured to shuttle a third suture 2200: through an posterior pin hole 1660, in a generally posterior to anterior direction; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. The third suture needle 2250 may be configured to disengage from the third suture 2200 leaving the ends of the third suture 2200 exterior to a patient and a central portion of the third suture 2200 tracing a path through the tendon repair instrument 1000.

In an embodiment, a fourth suture needle 2350 may be configured to shuttle a fourth suture (not shown): through an posterior pin hole 1660, in a generally posterior to anterior direction; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. The fourth suture needle 2350 may be configured to disengage from the fourth suture (not shown) leaving the ends of the fourth suture (not shown) exterior to a patient and a central portion of the fourth suture (not shown) tracing a path through the tendon repair instrument 1000.

In an embodiment, a fifth suture needle (not shown) may be configured to shuttle a fifth suture (not shown): through an posterior pin hole 1660, in a generally posterior to anterior direction; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. The fifth suture needle (not shown) may be configured to disengage from the fifth suture (not shown) leaving the ends of the fifth suture (not shown) exterior to a patient and a central portion of the fifth suture (not shown) tracing a path through the tendon repair instrument 1000.

In an embodiment, a tendon repair instrument 1000 may include a posterior pin guide 1600 including a first sidewall 1610 and a second sidewall 1620. The first sidewall 1610 may include a plurality of posterior pin holes 1660. The second sidewall may include a plurality of posterior pin holes 1660. The plurality of posterior pin holes 1660 may be configured to guide a plurality of suture needles in a generally anterior to posterior trajectory. Each of the plurality of posterior pin holes 1660 may be configured to have a suture needle trajectory angle 2500 that may be offset at least 10° from a coronal plane 2600.

The plurality of posterior pin holes 1660 may be configured to guide a plurality of suture needles: through a posterior pin hole 1660, in a generally anterior to posterior direction; through the skin and soft tissue of a patient; through one of a lateral tendon guide eye 1250 and a medial tendon guide eye 1350; through a tendon 1050, retained between a posterior tendon guide 1500 and an anterior tendon guide 1400, and retained between a lateral tendon guide 1200 and a medial tendon guide 1300; through a gap between the posterior tendon guide 1500 and the other of the lateral tendon guide 1200 and the medial tendon guide 1300; and exiting a patient through the soft tissue and skin.

The plurality of posterior pin holes 1660 may be configured to guide a plurality of suture needles: through a posterior pin hole 1660, in an at least partially posterior direction; through the skin and soft tissue of a patient; through one of a lateral tendon guide eye 1250 and a medial tendon guide eye 1350; through a tendon 1050, retained between a posterior tendon guide 1500 and an anterior tendon guide 1400, and retained between a lateral tendon guide 1200 and a medial tendon guide 1300; through a gap between the posterior tendon guide 1500 and the other of the lateral tendon guide 1200 and the medial tendon guide 1300; and exiting a patient through the soft tissue and skin.

The first sidewall 1610 and/or the second sidewall 1620 may be extended sufficiently anterior that one or more posterior pin holes 1660 can be anterior to the coronal plane 2600, enabling insertion of the suture needle(s) along a direction offset by at least 10° from the coronal plane 2600. The top surface 1650 may optionally be omitted, or may have corresponding holes that receive and further guide the suture needle(s). Additionally, or alternatively, the first sidewall 1610 and/or the second sidewall 1620 may have pin holes (not shown) that are positioned on the opposite side of the Achilles tendon from the posterior pin holes 1660, and receive and further guide the suture needle(s) after passage of the suture needle(s) through the Achilles tendon.

In some embodiments, the first sidewall 1610 and/or the second sidewall 1620 may extend further anteriorly and posteriorly of the coronal plane 2600 than is shown in the drawings in order to position such pin holes with the necessary offsets anteriorly and posteriorly of the coronal plane 2600. The top surface 1650 then may not be present, or may not have pin holes. In some embodiments, the suture needle(s) may be inserted posterior-to-anterior rather than anterior-to-posterior.

In an embodiment, each of the posterior pin holes 1660, the lateral pin guide 1630, and the medial pin guide 1635 may be configured so that the trajectories of any pair of guides do not intersect. Each of the posterior pin holes 1660, the lateral pin guide 1630, and the medial pin guide 1635 may be configured so that each of the first suture needle 2050; second suture needle 2150; third suture needle 2250; fourth suture needle 2350; and fifth suture needle (not shown) may be engaged with the tendon repair instrument 1000 without interference from a secondary suture needle.

Figure 24:
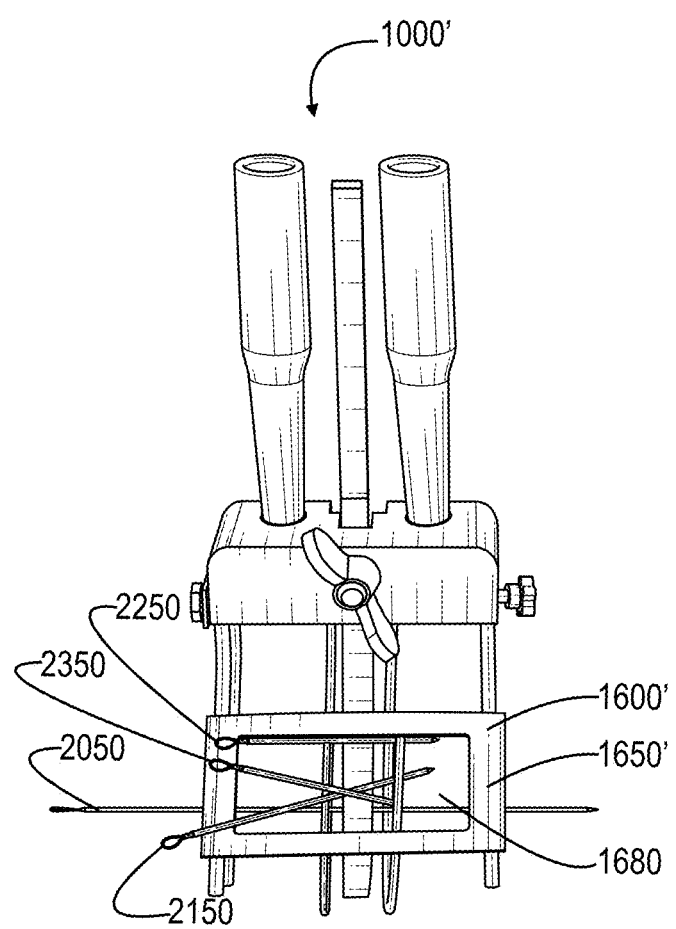
FIG. 24 is a perspective view of an instrument for surgical repair of an Achilles tendon with suture needles according to an embodiment.
Figure 25:
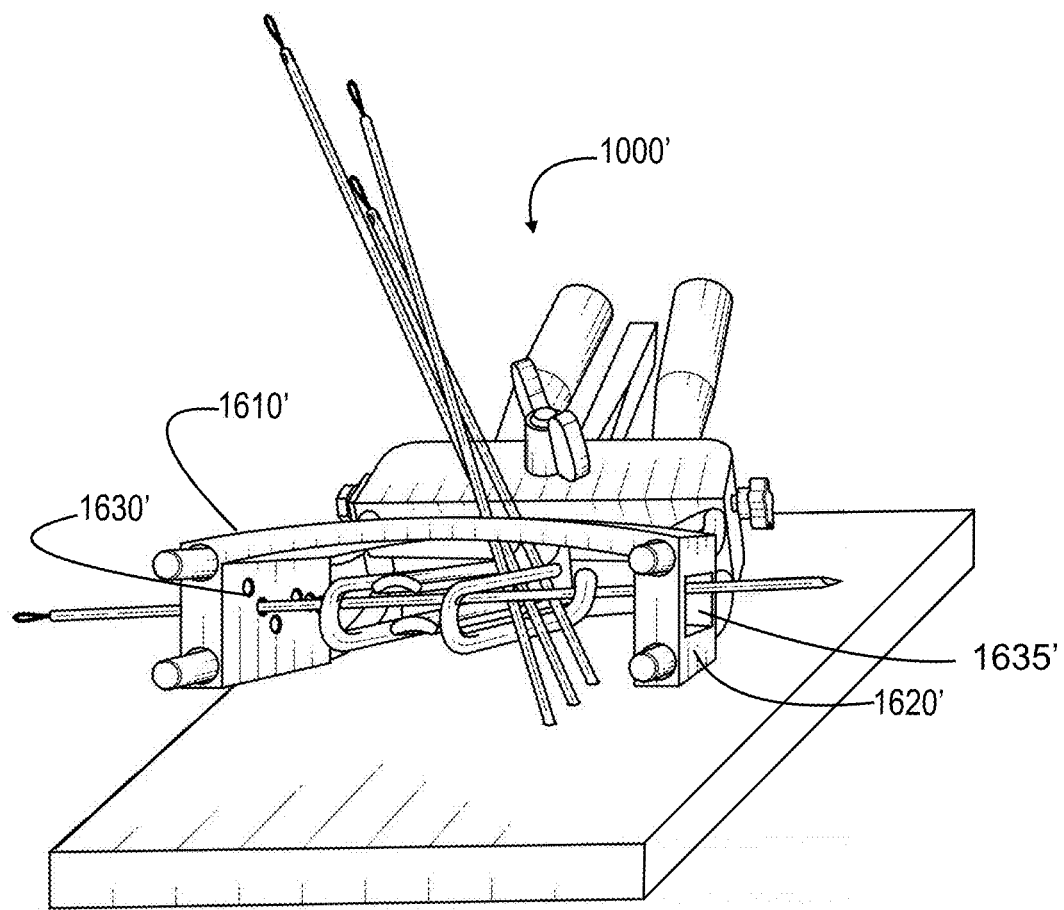
FIG. 25 is a perspective view of the instrument for surgical repair of an Achilles tendon of FIG. 24 with suture needles.

FIG. 24 and FIG. 25 show perspective views of an instrument for surgical repair of an Achilles tendon, or tendon repair instrument 1000' according to an embodiment. The tendon repair instrument 1000' may include a posterior pin guide 1600'. The posterior pin guide 1600' may include a first sidewall 1610', a second sidewall 1620', a plurality of lateral pin guides 1630', and a plurality of medial pin guides 1635'. The lateral pin guides 1630' may be configured to guide a plurality of suture needles through the second sidewall 1620' generally parallel to a coronal plane 2600. The medial pin guides 1635' may be configured to guide a plurality of suture needles through the first sidewall 1610' generally parallel to a coronal plane 2600. The lateral pin guides 1630' and the medial pin guides 1635' may be configured to guide a plurality of suture needles through a tendon 1050 between a posterior tendon guide 1500 and an anterior tendon guide 1400 with the tendon 1050 retained between the posterior tendon guide 1500 and the anterior tendon guide 1400.

The first sidewall 1610' and the second sidewall 1620' may include a plurality of lateral pin guides 1630' and medial pin guides 1635'. The medial pin guides 1635' may be configured to guide a plurality of suture needles through the first sidewall 1610' generally parallel to a coronal plane 2600. The lateral pin guides 1630' may be configured to guide a plurality of suture needles through the second sidewall 1620' generally parallel to a coronal plane 2600. The lateral pin guides 1630' and the medial pin guides 1635' may be configured to guide a plurality of suture needles through a tendon 1050 between a posterior tendon guide 1500 and an anterior tendon guide 1400 with the tendon 1050 retained between the posterior tendon guide 1500 and the anterior tendon guide 1400.

The posterior pin guide 1600' may further include a top surface 1650' including a top surface aperture 1680. The top surface aperture 1680 may take the place of the posterior pin holes 1660, and may be configured to allow a plurality of suture needles to pass: through the top surface aperture 1680; through the skin and soft tissue of a patient; through a gap between a posterior tendon guide 1500 and one of a lateral tendon guide 1200 and a medial tendon guide 1300; through a tendon 1050, retained between the posterior tendon guide 1500 and the anterior tendon guide 1400, and retained between the lateral tendon guide 1200 and the medial tendon guide 1300; through one of a lateral tendon guide eye 1250 and a medial tendon guide eye 1350; and exiting a patient through the soft tissue and skin. Each of the plurality of suture needles may have a trajectory that may be offset at least 15° from a coronal plane 2600.

In an embodiment, a lateral tendon guide 1200 and a medial tendon guide 1300 may be configured to engage a plurality of sutures that may follow the trajectories of a plurality of posterior pin holes 1660, a lateral pin guide 1630 and a medial pin guide 1635, and whose suture ends are exterior to a patient, whereby, when the lateral tendon guide 1200 and the medial tendon guide 1300 may be withdrawn from a surgical site through a percutaneous incision, the plurality of sutures may be engaged and the ends of the plurality of sutures may be drawn into the patient and then drawn back out of the patient through the percutaneous incision while leaving a central portion of each of the plurality of sutures engaged with the tendon 1050. The lateral tendon guide 1200 and the medial tendon guide 1300 may further be configured so that the lateral tendon guide 1200 and the medial tendon guide 1300 may disengage from the plurality of sutures through an opening in a lateral tendon guide eye 1250 and a medial tendon guide eye 1350.

In an embodiment, a lateral tendon guide 1200, a medial tendon guide 1300, a posterior tendon guide 1500, and an anterior tendon guide 1400 may be configured to permit routing of one or more suture needles through the tendon 1050 along trajectories that facilitate application of a Krackow suturing technique. The Krackow suturing technique is a continuous locking loop suture technique that may involve two or more locking loops placed along each side of a tendon and is well known in the art for open surgical tendon repair. The Krackow suturing technique may require suture needles to travel, at least partially, in a posterior to anterior direction.

Additionally, a plurality of posterior pin holes 1660, a lateral pin guide 1630, and a medial pin guide 1635 may be configured to permit insertion of one or more suture needles through the tendon 1050 along trajectories that facilitate application of the Krackow suturing technique. In an embodiment, a lateral tendon guide 1200, a medial tendon guide 1300, a posterior tendon guide 1500, and an anterior tendon guide 1400 may be configured to permit insertion of one or more suture needles through the tendon 1050 along trajectories that facilitate application of other suturing techniques used in open Achilles tendon repair surgery, such as McKeon's Double Krackow, Wilson's Double Krackow, Ostrander's Modified Krackow, Giftbox-modified Krackow, Kessler, or Bunnell.

Figure 26:
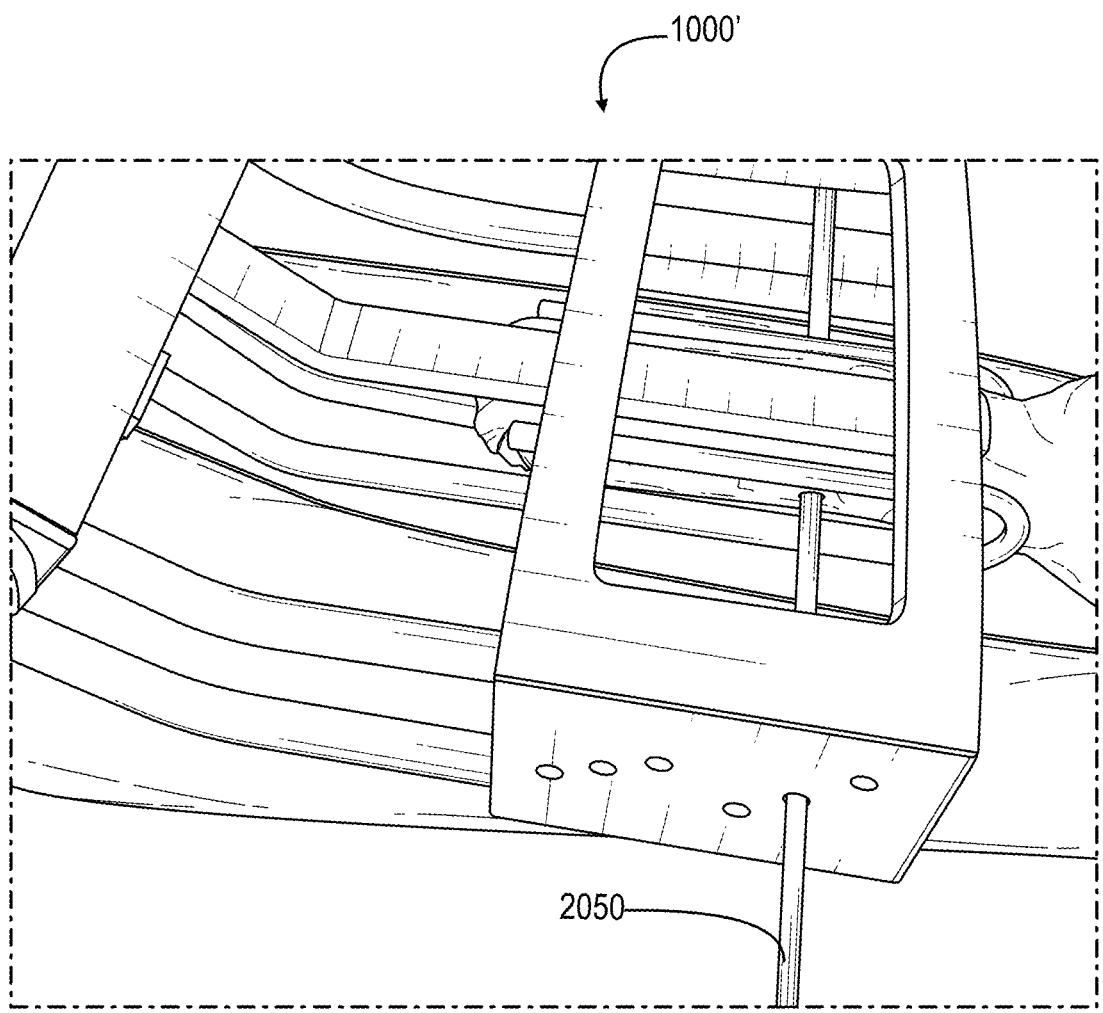
FIG. 26 is a perspective view of a step in a method for surgical repair of an Achilles tendon according to an embodiment.
Figure 27:
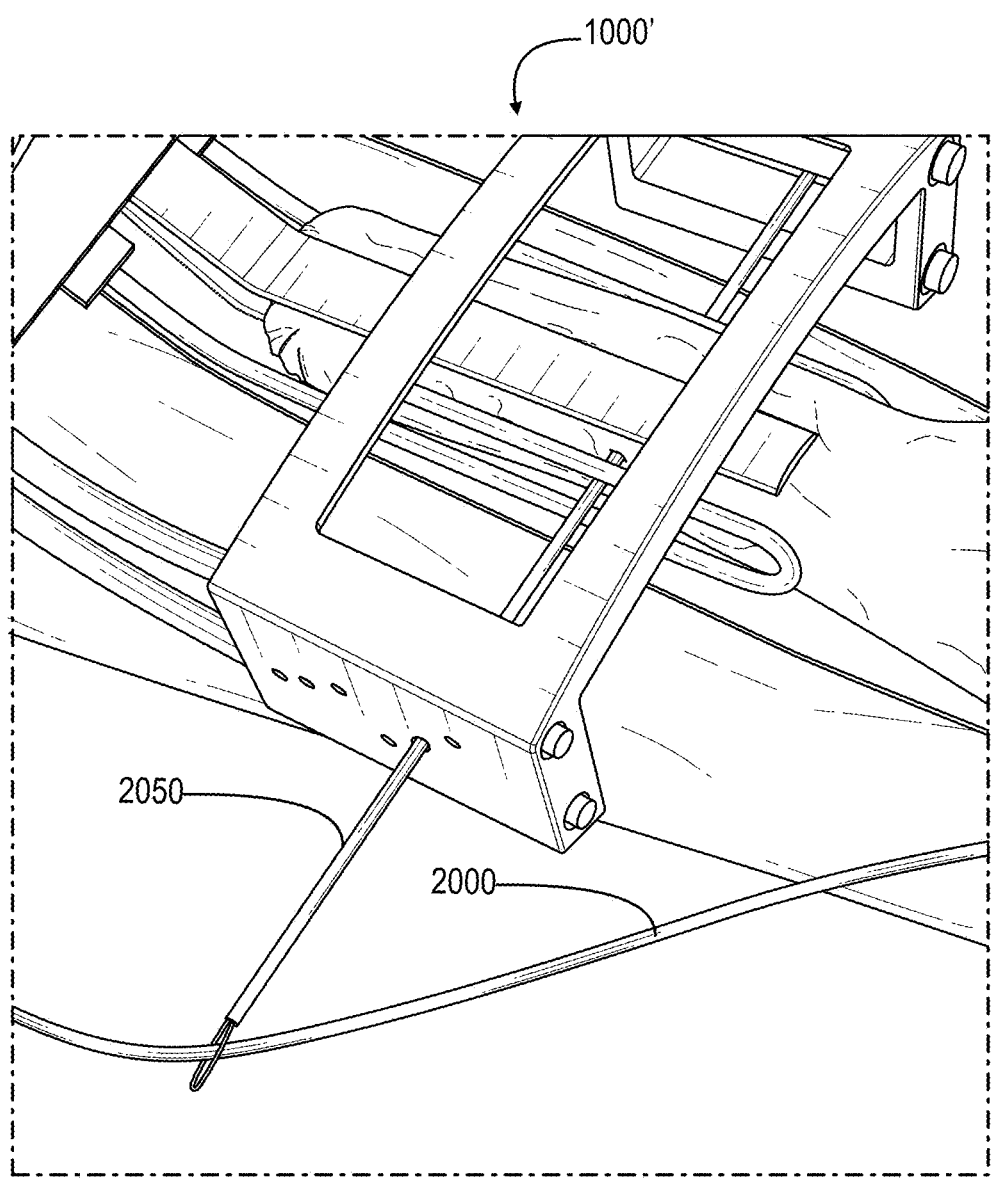
FIG. 27 is a perspective view of a step in a method for surgical repair of an Achilles tendon according to an embodiment.
Figure 28:
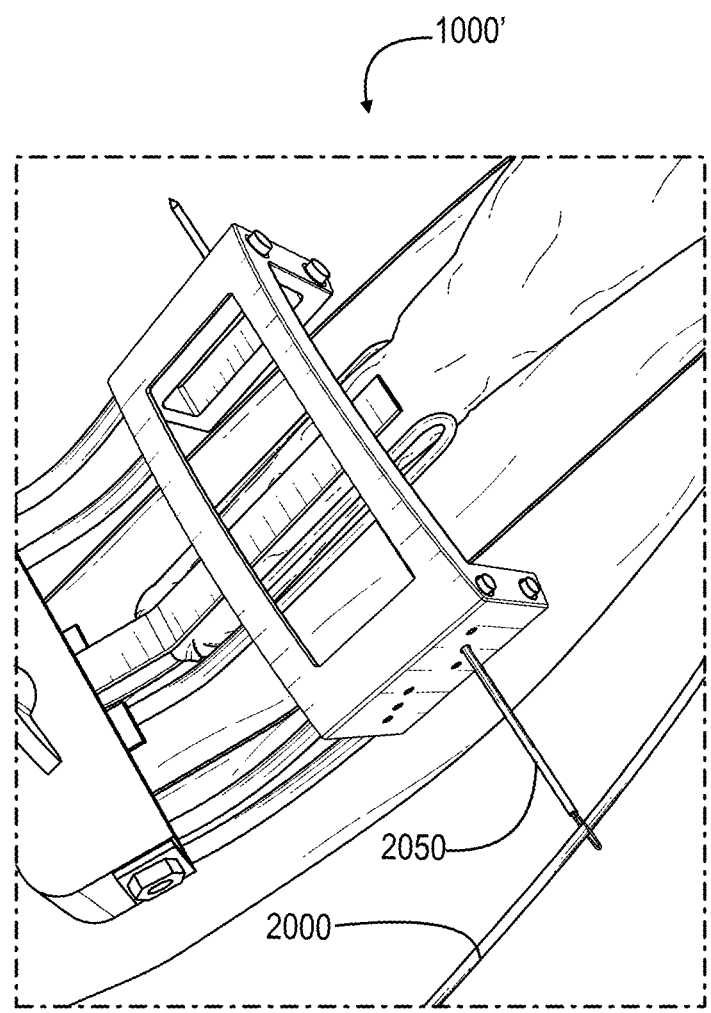
FIG. 28 is a perspective view of a step in a method for surgical repair of an Achilles tendon according to an embodiment.
Figure 29:
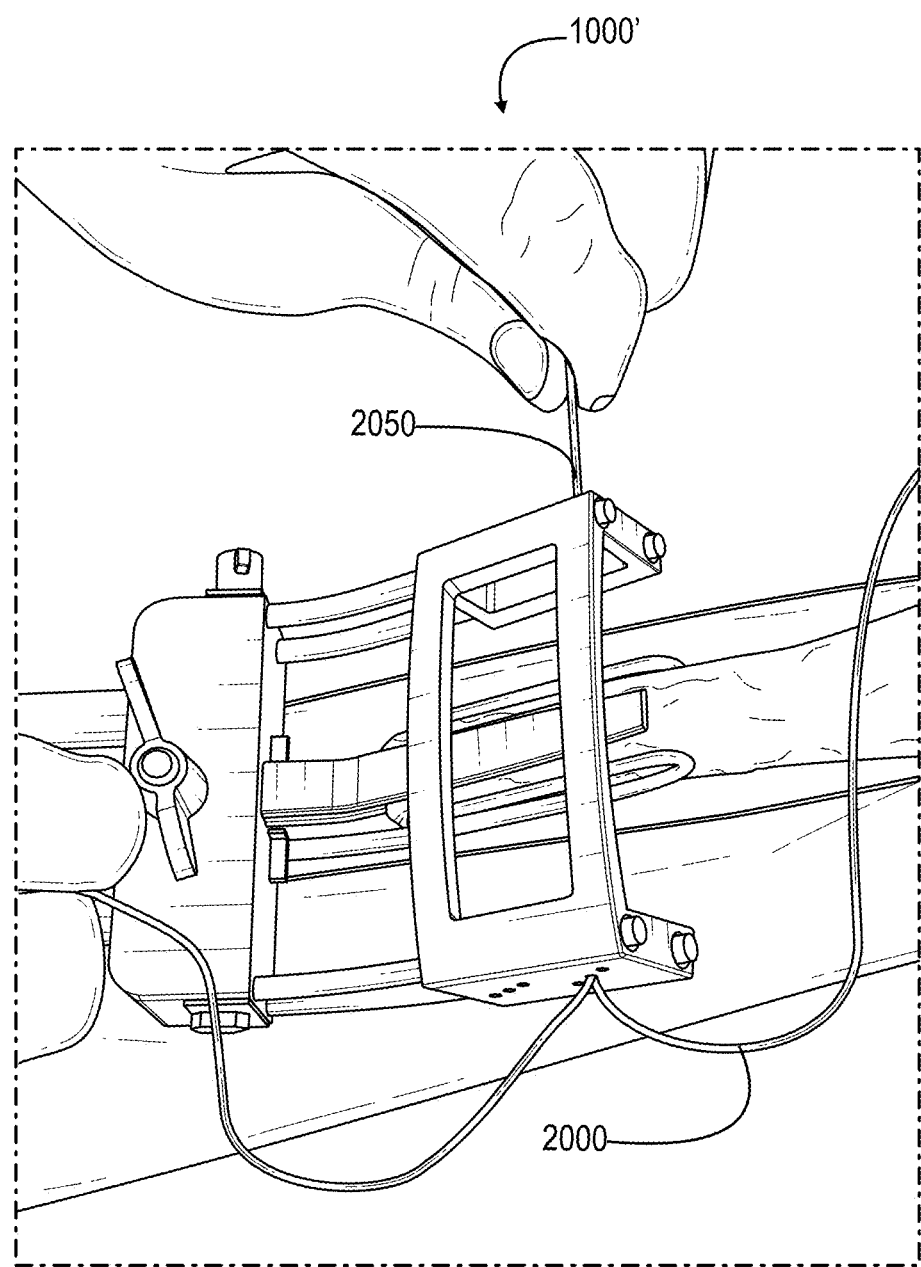
FIG. 29 is a perspective view of a step in a method for surgical repair of an Achilles tendon according to an embodiment.
Figure 30:
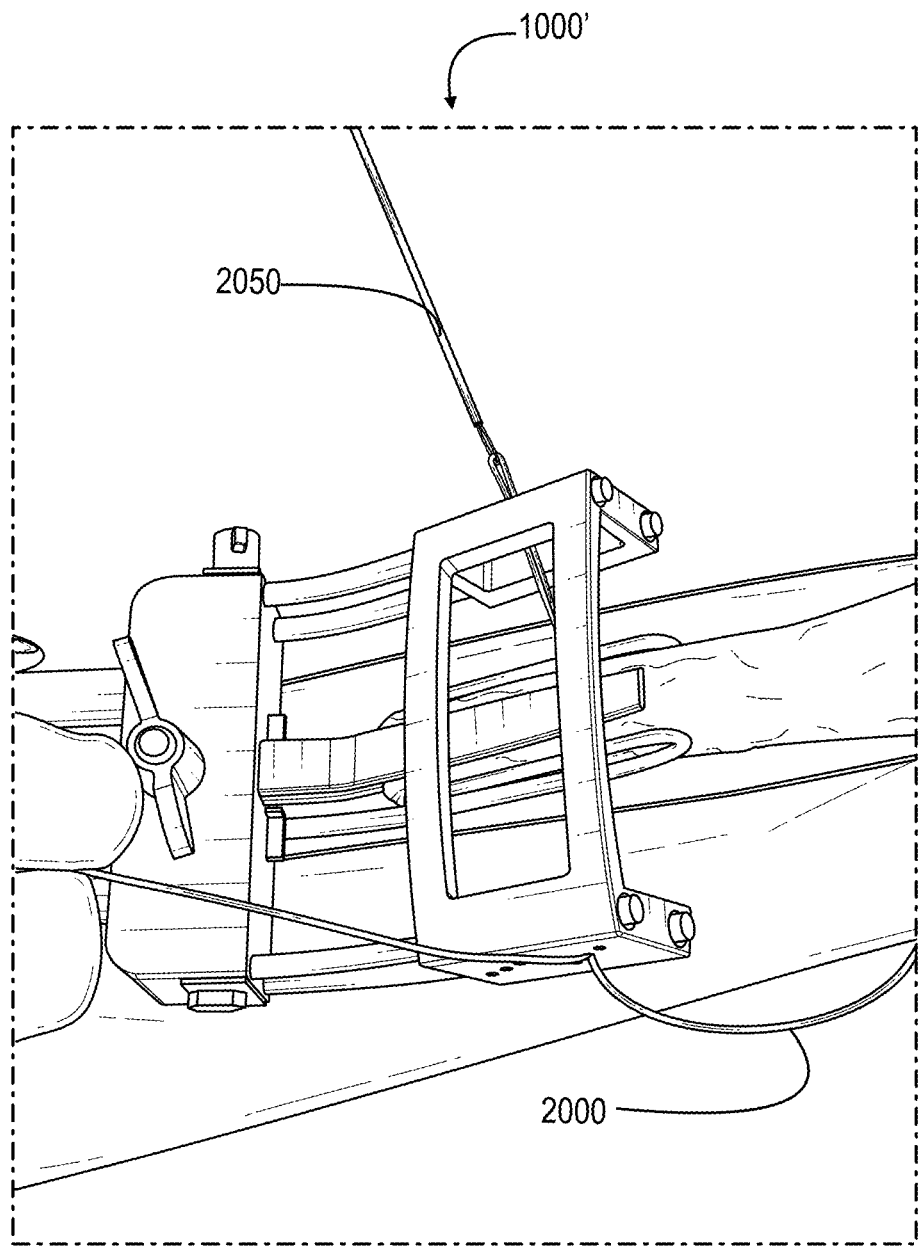
FIG. 30 is a perspective view of a step in a method for surgical repair of an Achilles tendon according to an embodiment.
Figure 31:
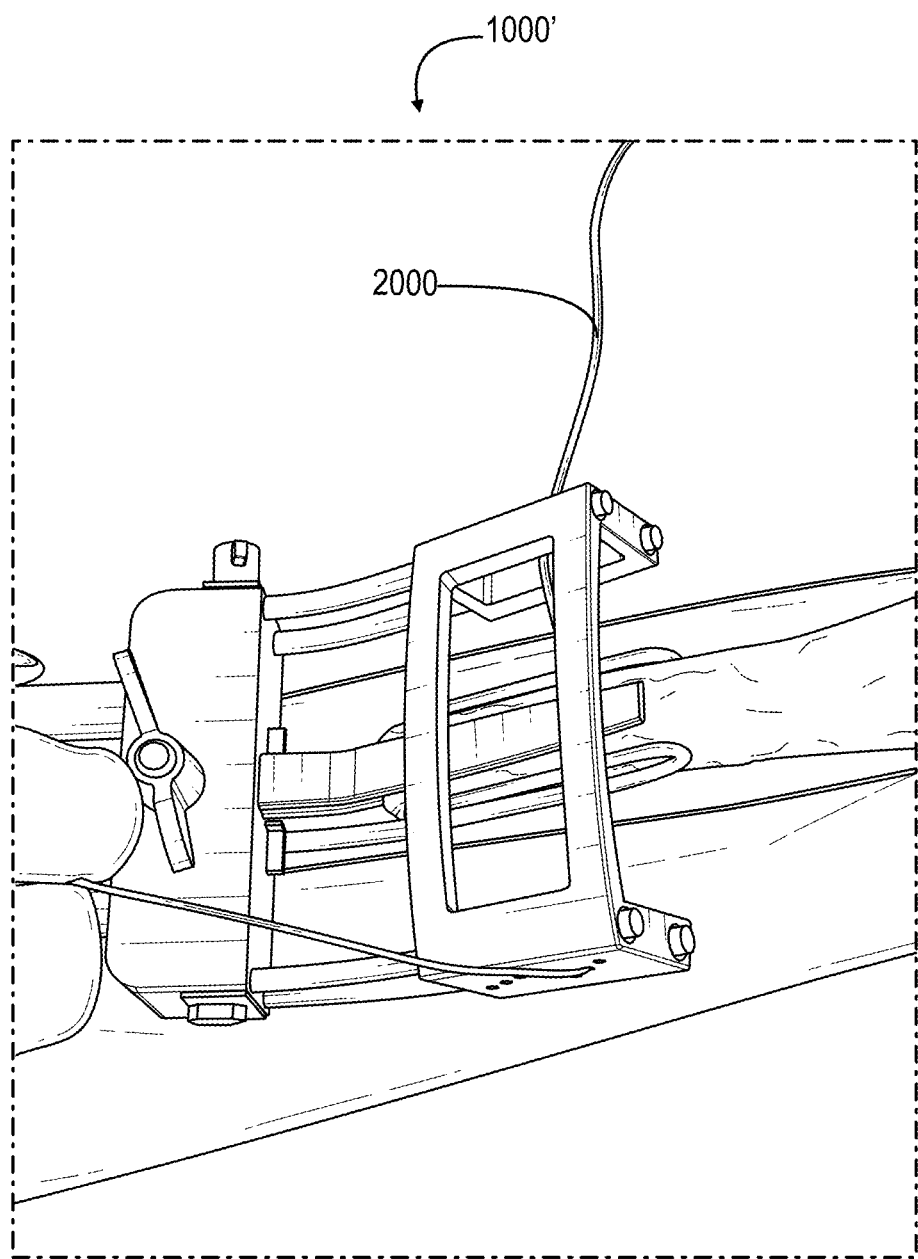
FIG. 31 is a perspective view of a step in a method for surgical repair of an Achilles tendon according to an embodiment.
Figure 32:
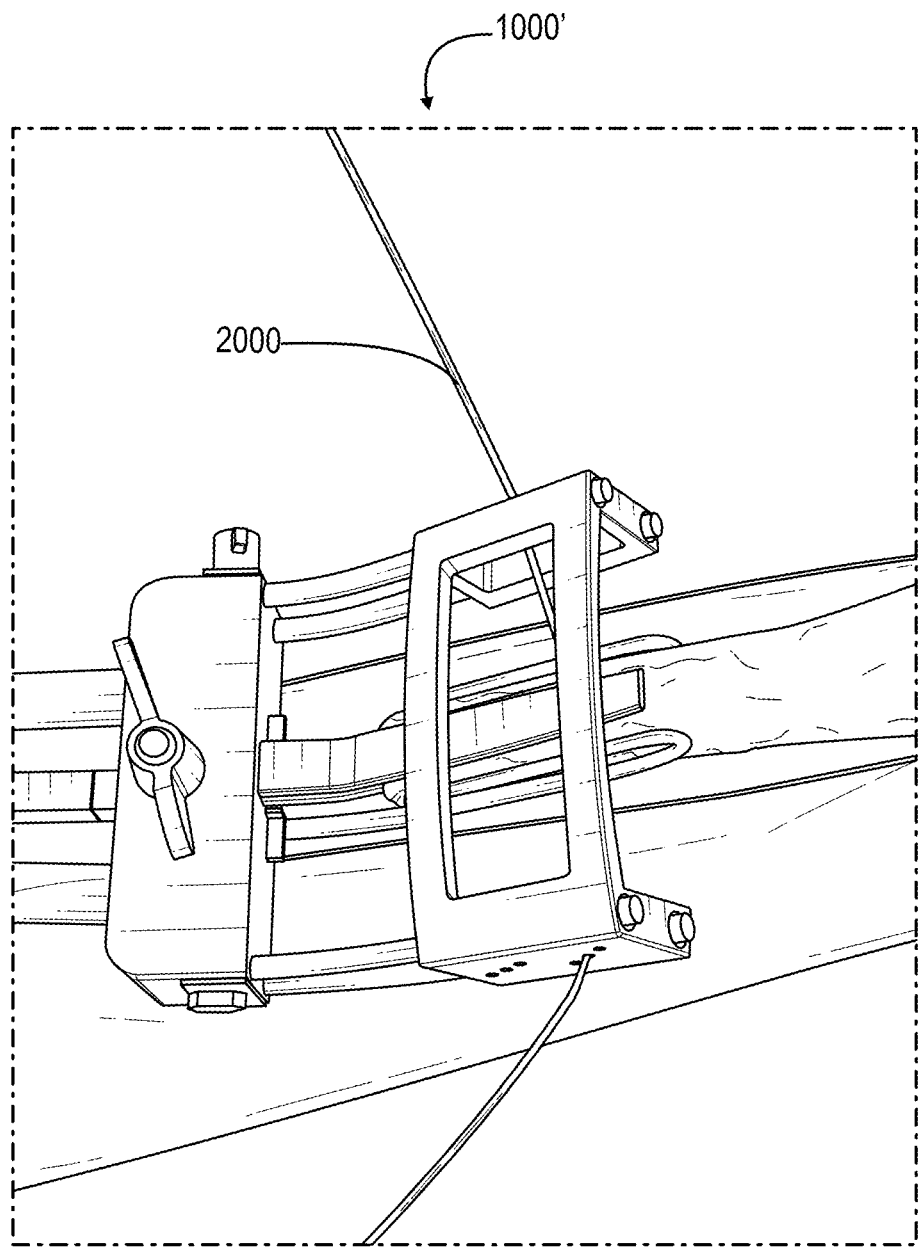
FIG. 32 is a perspective view of a step in a method for surgical repair of an Achilles tendon according to an embodiment.
Figure 33:
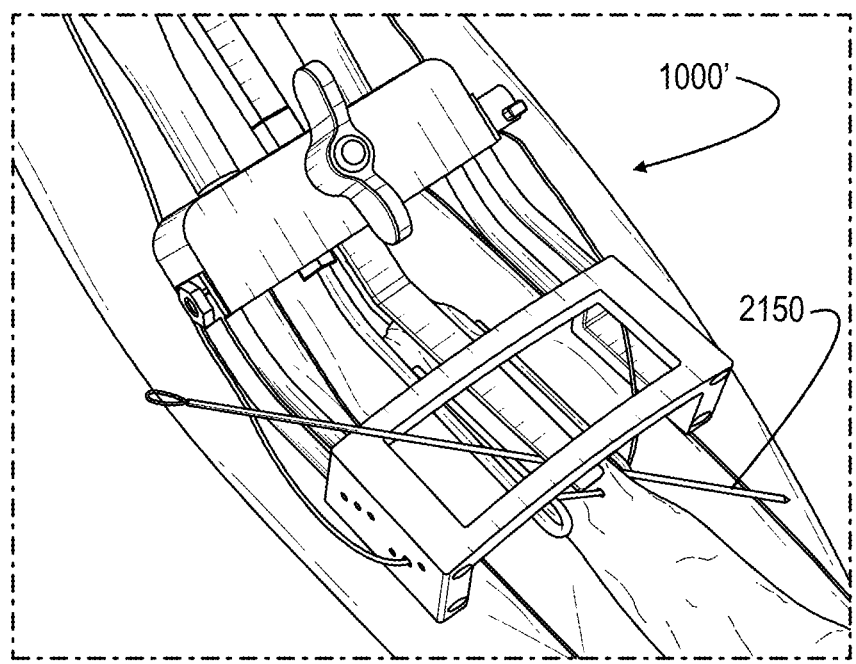
FIG. 33 is a perspective view of a step in a method for surgical repair of an Achilles tendon according to an embodiment.
Figure 34:
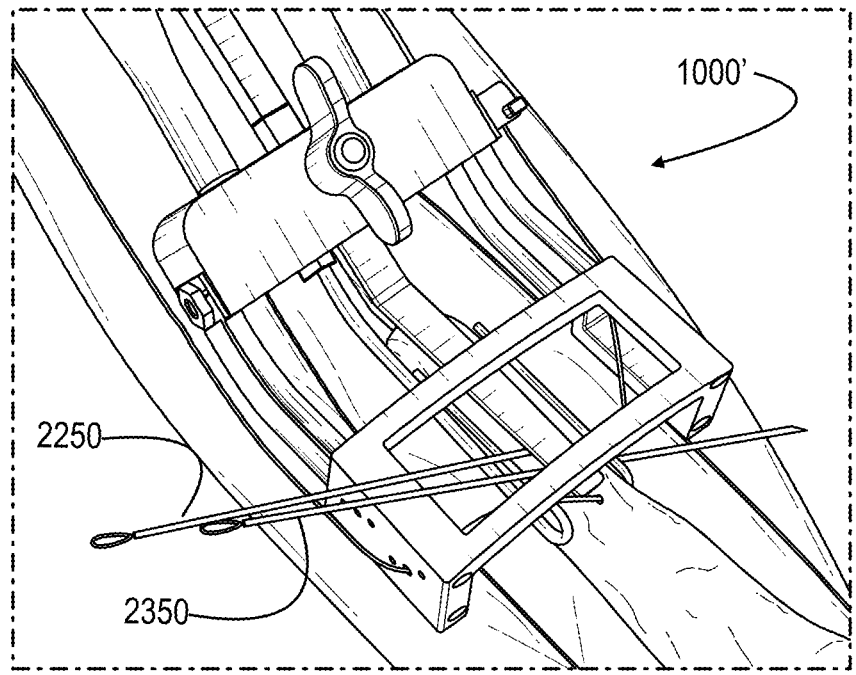
FIG. 34 is a perspective view of a step in a method for surgical repair of an Achilles tendon according to an embodiment.
Figure 35:
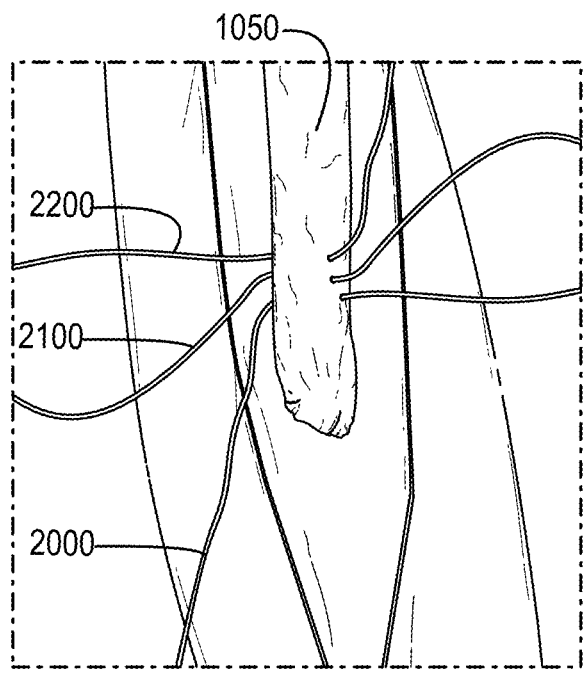
FIG. 35 is a perspective view of a step in a method for surgical repair of an Achilles tendon according to an embodiment.
Figure 36:
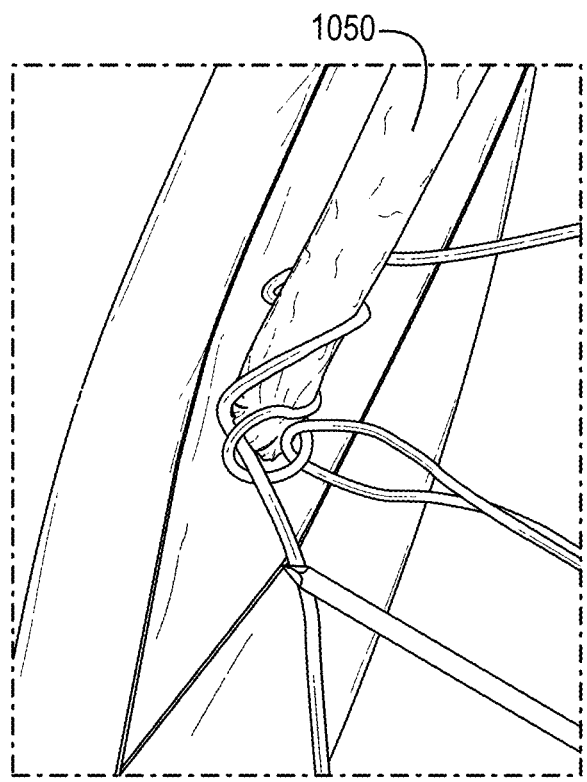
FIG. 36 is a perspective view of a step in a method for surgical repair of an Achilles tendon according to an embodiment.

FIG. 26 though FIG. 36 illustrate one exemplary method for minimally invasive percutaneous Achilles tendon repair surgery using a tendon repair instrument 1000 according to an embodiment. The method for minimally invasive percutaneous Achilles tendon repair surgery using a tendon repair instrument 1000 may include the following steps:

1. Make a percutaneous incision over the rupture site and enter the paratenon. Grab the free tendon with a snap or clamp.
2. Adjust the distance between the medial tendon guide and the lateral tendon guide, and the distance between the anterior tendon guide and the posterior tendon guide, so that the tendon repair instrument may be fully inserted along the Achilles tendon using the snap or clamp to hold the tendon stable.
3. Insert the arms of the tendon repair instrument into the paratenon of the Achilles tendon and maneuver the instrument to receive the Achilles tendon such that the Achilles tendon is retained between the medial tendon guide and the lateral tendon guide.
4. Optional step: The anterior tendon guide may optionally be attached to the device prior to insertion into the paratenon. If the anterior tendon guide is not attached, after the device is inserted, insert the anterior tendon guide along the anterior side of the Achilles tendon and, once fully inserted, secure it to the handle of the tendon repair instrument.
5. Actuate the anterior tendon guide to grip the tendon between the anterior tendon guide and the posterior tendon guide.
6. Pass a first suture needle through a medial pin guide and/or a lateral pin guide.
7. Leave the first suture needle in place while inserting subsequent suture needles to help hold the tendon in place.
8. Pass additional suture needles through the posterior pin holes, that are offset at least 100 from a coronal plane 2600, and into the tendon along directions that are at least partially anterior.
9. Pull suture needles through leaving approximately equal ends of sutures on both sides, exterior to the patient.
10. Adjust anterior tendon guide to release pressure on the tendon.
11. Withdraw tendon repair instrument from surgical site pulling ends of sutures out through the percutaneous incision.
12. Use suture ends and loops to perform Krackow suturing technique; Kessler suturing technique; Bunnell suturing technique; or other suturing technique commonly used in open Achilles tendon repair surgery.

The foregoing is just one of many possible methods in which an instrument according to the present disclosure may be employed. In one exemplary method for minimally invasive percutaneous Achilles tendon repair surgery using a tendon repair instrument 1000, the above method may include the following additional steps:

1. Perform steps 1-9 of the above method
2. Partially withdraw the tendon repair instrument so that the posterior pin guide is located between the previously placed sutures and the percutaneous incision. Ensure the posterior pin guide is located above the tendon.
3. Repeat steps 4-9 of the above method.
4. Perform steps 10-11 of the above method.

Those of skill in the art will recognize that this is only one of many potential methods that may be used for minimally invasive percutaneous Achilles tendon repair surgery. In alternative embodiments, different methods may be used to surgically repair an Achilles using a tendon repair instrument 1000 or other systems described above. Further, the method set forth in FIG. 26 through FIG. 36 may be employed to surgically repair an Achilles tendon using other tendon repair instruments besides those specifically disclosed herein.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

What is claimed is:

1. A method for surgical repair of an Achilles tendon, the method comprising:
    positioning an instrument proximate the Achilles tendon, the instrument comprising:
        a handle; and
        a plurality of tendon guides;
    maneuvering the instrument such that the plurality of tendon guides is positioned anteriorly, posteriorly, laterally, and medially of the Achilles tendon;
    actuating the plurality of tendon guides to retain the Achilles tendon between the plurality of tendon guides; and
    using the instrument to insert a suture through the Achilles tendon along one or more trajectories, each of which is offset at least 10° from a coronal plane.

2. The method of claim 1, wherein:
    the plurality of tendon guides comprises a medial tendon guide, a lateral tendon guide, an anterior tendon guide, and a posterior tendon guide; and
    maneuvering the instrument further comprises:
        positioning the medial tendon guide medially of the Achilles tendon;
        positioning the lateral tendon guide laterally of the Achilles tendon;
        positioning the anterior tendon guide anteriorly of the Achilles tendon; and
        positioning the posterior tendon guide posteriorly of the Achilles tendon.

3. The method of claim 1, wherein each of the one or more trajectories is offset at least 20° from the coronal plane.

4. The method of claim 1, the method further comprising:
    using the instrument to insert one or more sutures through the Achilles tendon such that the one or more sutures are routed according to a suturing technique used in open Achilles tendon repair surgery.

5. The method of claim 4, wherein the suturing technique is a Krackow suturing technique.

6. The method of claim 1, wherein the instrument further comprises:
    a posterior pin guide comprising one or more posterior pin holes.

7. The method of claim 6, wherein each of the one or more posterior pin holes is angularly offset from the coronal plane and parallel to at least one of the one or more trajectories.

8. The method of claim 6, wherein the posterior pin guide further comprises a lateral pin guide and a medial pin guide that guide a pin parallel to the coronal plane.

9. The method of claim 6, the method further comprising:
    inserting one or more pins through the one or more posterior pin holes and into the Achilles tendon along directions that are at least partially anterior.

10. A method for surgical repair of an Achilles tendon, the method comprising:
    positioning an instrument proximate the Achilles tendon, the instrument comprising:
        a handle;
        a medial tendon guide;
        a lateral tendon guide;
        an anterior tendon guide;
        a posterior tendon guide; and
        a posterior pin guide comprising one or more posterior pin holes;
    maneuvering the instrument to receive the Achilles tendon such that the Achilles tendon is retained between the medial tendon guide and the lateral tendon guide; and
    actuating the anterior tendon guide to grip the Achilles tendon between the posterior tendon guide and the anterior tendon guide.

11. The method of claim 10, the method further comprising:
    inserting one or more pins through the one or more posterior pin holes and into the Achilles tendon along directions that are at least partially anterior.

12. The method of claim 10, the method further comprising:
    maneuvering the instrument to receive the Achilles tendon such that the Achilles tendon is retained between the medial tendon guide and the lateral tendon guide at a first location along the Achilles tendon;
    actuating the anterior tendon guide to grip the Achilles tendon between the posterior tendon guide and the anterior tendon guide at the first location;
    using the instrument to insert a first suture through the Achilles tendon along one or more trajectories;
    releasing the Achilles tendon from the instrument;
    partially withdrawing the instrument so that the posterior pin guide is located between the first suture and a percutaneous incision;
    maneuvering the instrument to receive the Achilles tendon such that the Achilles tendon is retained between the medial tendon guide and the lateral tendon guide at a second location along the Achilles tendon; and
    using the instrument to insert a second suture through the Achilles tendon along one or more trajectories.

13. The method of claim 12, wherein each of the one or more trajectories is offset at least 10° from a coronal plane.

14. The method of claim 12, wherein each of the one or more trajectories is offset at least 15° from a coronal plane.

15. The method of claim 10, the method further comprising:
    using the instrument to insert one or more sutures through the Achilles tendon such that the one or more sutures are routed according to a Krackow suturing technique.

16. A method for surgical repair of an Achilles tendon, the method comprising:
positioning an instrument proximate the Achilles tendon, the instrument comprising:
a handle;
a plurality of tendon guides; and
at least one pin guide selected from a group consisting of a lateral pin guide and
a medial pin guide;
maneuvering the instrument such that the plurality of tendon guides is positioned anteriorly, posteriorly, laterally, and medially of the Achilles tendon;
actuating the plurality of tendon guides to retain the Achilles tendon between the plurality of tendon guides; and
inserting one or more pins through one or more pin holes of the at least one pin guide and into the Achilles tendon along an at least partially anterior direction offset from a coronal plane by at least 10° or an at least partially posterior direction offset by the coronal plane by at least 10°.

17. The method of claim 16, wherein:
the plurality of tendon guides comprises a medial tendon guide, a lateral tendon guide, an anterior tendon guide, and a posterior tendon guide; and
maneuvering the instrument further comprises:
positioning the medial tendon guide medially of the Achilles tendon;
positioning the lateral tendon guide laterally of the Achilles tendon;
positioning the anterior tendon guide anteriorly of the Achilles tendon; and
positioning the posterior tendon guide posteriorly of the Achilles tendon.

18. The method of claim 16, wherein at least one of the one or more pin holes is positioned anterior to the coronal plane and an axis of the at least one of the one or more pin holes is posteriorly offset from the coronal plane by at least 10°.

19. The method of claim 16, wherein at least one of the one or more pin holes is positioned posterior to the coronal plane and an axis of the at least one of the one or more pin holes is anteriorly offset from the coronal plane by at least 10°.

20. The method of claim 16, the method further comprising:
using the one or more pins to guide one or more sutures through the Achilles tendon along the at least partially anterior direction or the at least partially posterior direction.

* * * * *